US007968723B2

(12) United States Patent
Havranek et al.

(10) Patent No.: US 7,968,723 B2
(45) Date of Patent: Jun. 28, 2011

(54) COMPOUNDS, THEIR PREPARATION AND USE

(75) Inventors: Miroslav Havranek, Prague (CZ); Per Sauerberg, Farum (DK); Ingrid Pettersson, Frederiksberg (DK); Pavel Pihera, Prague (CZ); Soren Ebdrup, Roskilde (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 459 days.

(21) Appl. No.: 11/579,712

(22) PCT Filed: May 3, 2005

(86) PCT No.: PCT/EP2005/052014
§ 371 (c)(1),
(2), (4) Date: Oct. 9, 2008

(87) PCT Pub. No.: WO2005/105726
PCT Pub. Date: Nov. 10, 2005

(65) Prior Publication Data
US 2009/0209588 A1 Aug. 20, 2009

(30) Foreign Application Priority Data
May 5, 2004 (DK) .................................. 2004 00719

(51) Int. Cl.
C07D 213/00 (2006.01)
A01N 43/78 (2006.01)
(52) U.S. Cl. ........ 546/264; 548/204; 548/504; 514/332; 514/365; 514/426
(58) Field of Classification Search .................. 548/204, 548/504; 514/365, 426, 332; 546/264
See application file for complete search history.

(56) References Cited

U.S. PATENT DOCUMENTS

| | | | |
|---|---|---|---|
| 4,920,132 A | 4/1990 | Huang et al. | |
| 5,324,743 A | 6/1994 | Dillard et al. | |
| 5,538,768 A | 7/1996 | Marden et al. | |
| 6,448,293 B1 | 9/2002 | Andrews et al. | |
| 6,525,094 B1 | 2/2003 | Zhang et al. | |
| 6,630,504 B2 | 10/2003 | Andrews et al. | |
| 6,869,975 B2 | 2/2005 | Abe et al. | |
| 6,875,780 B2 | 4/2005 | Auerbach et al. | |
| 6,939,875 B2 | 9/2005 | Auerbach et al. | |
| 6,964,983 B2 | 11/2005 | Auerbach et al. | |
| 7,244,763 B2 | 7/2007 | Bratton et al. | |
| 7,816,385 B2 | 10/2010 | Sauerberg et al. | |
| 2001/0041709 A1 | 11/2001 | Mogensen et al. | |
| 2004/0192743 A1* | 9/2004 | Mjalli et al. | |
| 2004/0209936 A1* | 10/2004 | Bratton et al. | |
| 2005/0113440 A1 | 5/2005 | Auerbach et al. | |
| 2007/0082907 A1* | 4/2007 | Canada et al. | |
| 2009/0048257 A1* | 2/2009 | Sauerberg et al. | |
| 2009/0192162 A1* | 7/2009 | Ebdrup | |

FOREIGN PATENT DOCUMENTS

| | | | |
|---|---|---|---|
| GB | 2279659 | * | 1/1995 |
| JP | 2003-171275 | | 6/2003 |
| WO | 97/27847 | | 8/1997 |
| WO | 97/27857 | | 8/1997 |
| WO | 97/28115 | | 8/1997 |
| WO | 97/28137 | | 8/1997 |
| WO | 97/28149 | | 8/1997 |
| WO | 98/27974 | | 7/1998 |
| WO | 99/04815 | | 2/1999 |
| WO | WO 99/20275 | | 4/1999 |
| WO | 01/00603 | | 1/2001 |
| WO | 01/25181 | | 4/2001 |
| WO | WO 01/25226 | | 4/2001 |
| WO | WO 02/28434 | | 4/2001 |
| WO | WO 01/34137 | | 5/2001 |
| WO | WO 01/34200 | | 5/2001 |
| WO | WO 01/60807 | | 8/2001 |
| WO | WO 01/66098 | | 9/2001 |
| WO | 01/79197 | | 10/2001 |
| WO | 02/14291 | | 2/2002 |
| WO | 02/46154 | | 6/2002 |
| WO | WO 02/50048 | | 6/2002 |
| WO | WO 02/053547 | | 7/2002 |
| WO | 02/59098 | | 8/2002 |
| WO | WO 02/062774 | | 8/2002 |
| WO | WO 02/070011 | | 9/2002 |
| WO | 02/076957 | | 10/2002 |
| WO | 02/079162 | | 10/2002 |
| WO | 02/080899 | | 10/2002 |

(Continued)

OTHER PUBLICATIONS

Schiffrin et. al., "Peroxisome Proliferator-Activated Receptors: Vascular and Cardiac Effects in Hypertension", Hypertension, 2003, 42; pp. 664-668.*
Chilonczyk et. al., "Hypolipidaemic and antiplatelet agents", 2001, Expert Opin. Ther. Patents, 11 (8), pp. 1301-1327.*
Berger, J et al—The J of Biological Chem—1999—vol. 274—Part 10—pp. 6718-6725.
Leibowitz. M.D. et al—F E B S Lett—2000—vol. 473—pp. 333-336.
Oliver. W.R. et al—PNAS—2001—vol. 98—Part 9—pp. 5306-5311.
Muoio. D.M. et al—The J of Biological Chem—2002—vol. 277—Part 29-pp. 26089-26097.
Wang. Y-X et al—Cell—2003—vol. 113—pp. 159-170.

(Continued)

*Primary Examiner* — Janet Andres
*Assistant Examiner* — Heidi Reese
(74) *Attorney, Agent, or Firm* — Robert S. Dailey

(57) ABSTRACT

Novel compounds of the general formula (I), in which the variables are as defined in claim 1, the use of these compounds as pharmaceutical compositions, pharmaceutical compositions comprising the compounds and methods of treatment employing these compounds and compositions. The present compounds are useful in the treatment and/or prevention of conditions mediated by Peroxisome Proliferator-Activated Receptors (PPAR), in particular the PPARδ subtype, namely, type 1 diabetes, type 2 diabetes, dyslipidaemia, syndrome X (including the metabolic syndrome, i.e. impaired glucose tolerance, insulin resistance, hyper-triglyceridaemia and/or obesity), cardiovascular diseases (including atherosclerosis) and hypercholesterolaemia.

52 Claims, No Drawings

FOREIGN PATENT DOCUMENTS

| WO | 02/098840 | 12/2002 |
|---|---|---|
| WO | 02/100812 | 12/2002 |
| WO | WO 03/002081 | 1/2003 |
| WO | 03/016265 | 2/2003 |
| WO | 03/016291 | 2/2003 |
| WO | WO 03/024395 | 3/2003 |
| WO | 03/033493 | 4/2003 |
| WO | WO 03/033453 | 4/2003 |
| WO | 03/035603 | 5/2003 |
| WO | 03/072100 | 9/2003 |
| WO | 03/074050 | 9/2003 |
| WO | 03/074051 | 9/2003 |
| WO | 03/074052 | 9/2003 |
| WO | WO 03/074495 | 9/2003 |
| WO | 03/084916 | 10/2003 |
| WO | 2003/084916 * | 10/2003 |
| WO | 03/097607 | 11/2003 |
| WO | WO 2004/000315 | 12/2003 |
| WO | WO 2004/000762 | 12/2003 |
| WO | 2004/005253 | 1/2004 |
| WO | WO 2004/007439 | 1/2004 |
| WO | 2004/022533 | 3/2004 |
| WO | 2004/056740 * | 7/2004 |
| WO | WO 2004/060871 | 7/2004 |
| WO | WO 2004/063165 | 7/2004 |
| WO | WO 2004/063166 | 7/2004 |
| WO | 2004/071447 * | 8/2004 |
| WO | WO 2004/073606 | 9/2004 |
| WO | WO 2004/080943 | 9/2004 |
| WO | WO 2004/080947 | 9/2004 |
| WO | WO 2004/092117 | 10/2004 |
| WO | WO 2004/093879 | 11/2004 |
| WO | WO 2004/099170 | 11/2004 |
| WO | WO 2005/054176 | 6/2005 |
| WO | WO 2005/097098 | 10/2005 |
| WO | WO 2005/097762 | 10/2005 |
| WO | WO 2005/097763 | 10/2005 |
| WO | WO 2005/113506 | 12/2005 |
| WO | 2007/003581 | 1/2007 |
| WO | WO 2007/003581 | 1/2007 |
| WO | 2007/101864 | 9/2007 |

OTHER PUBLICATIONS

Luquet. S et al—Faseh J—2003—vol. 17—Part 13—pp. 209-226.
Tanaka. T et al—PNAS—2003—vol. 100—Part 26—pp. 15924-15929.
Holst, D et al—Biochem Biophys Acta—2003—vol. 1633 —pp. 43-50.
Dressel, U et al—Mol Endocrinol—2003—vol. 17—Part 12—pp. 2477-2493.
Lee, C-H et al—Science—2003—vol. 32—pp. 453-457.
International Search Report for PCT/EP05/052014, dated Sep. 16, 2005.
International Preliminary Report on Patentability for PCT/EP05/052014, dated Nov. 16, 2006.
Berger, J. and Wagner, J., "Physiological and Therapeutic Roles of Peroxisome Proliferator-Activated Receptors," Diabetes Technology & Therapeutics, vol. 4(2), pp. 163-174 (2002).
Colagiuri et al., American Journal of Public Health, Sep. 2006, vol. 96, No. 9, pp. 1562-1569.
Curtis et al., The Journal of the American Board of Family Practice, vol. 18, pp. 37-43, (2005).
Epple et al., Bioorganic & Medicinal Chemistry Letters 2006, 16, 4376-4380.
Everett, L., et al., "The role of hepatic peroxisome proliferator-activated receptors (PPARs) in health and disease," Liver, vol. 20, pp. 191-199 (2000).
Fruchart, J., "PPAR and Cardiovascular Risk: Overview," J. Cardiovasc. Risk, vol. 8(4), pp. 185-186 (Aug. 2001).
Golub et al., Science, vol. 286, Oct. 15, 1999, pp. 531-537.
Gross et al., Best Practice & Research Clinical Endocrinology & Metabolism 2007, 21, 687-710.
Havranek et al., "E/Z Isomerization of 3,3-disubstituted allylic thioethers" Tetrahedron Lett., vol. 48,. pp. 6970-6973 (2007).
Hussain et al., Diabetes Research and Clinical Practice 2007, 76, 317-326.
Jones, B., "Peroxisome Proliferative-Activated Receptor (PPAR) Modulators: Diabetes and Beyond," Medicinal Research Reviews, vol. 21(6), pp. 540-552 (Nov. 2001).
Kaplan, F., et al., "PPARs, Insulin Resistance and Type 2 Diabetes," J. Cardiovasc. Risk, vol. 8(4), pp. 211-217 (Aug. 2001).
Kersten, S., et al., "Roles of PPARs in health and disease," Nature, vol. 405, pp. 421-424 (May 2000).
Landreth et al., Neurobiology of Aging, 2001, 22, 937-944.
Lee, C.H. et al., "PPAR-delta regulates glucose metabolism and insulin sensitivity", Proceedings of the National Academy of Sciences of the USA, 2006, vol. 103, No. 9, pp. 3444-3449.
Liu, K., et al., "Identification of a Series of PPAR gamma/delta Dual Agonists via Solid-Phase Parallel Synthesis," Bioorg. Med. Chem. Lett., vol. 11, pp. 2959-2962 (Nov. 2001).
Michalik, L., and Wahli, W., "Peroxisome proliferator-activated receptors: three isotypes for a multitude of functions," Curr. Opin. Biotechnology, vol. 10, pp. 564-570 (1999).
Miller, A., and Etgen, G., "Novel peroxisome proliferator-activated receptor ligands for type 2 diabetes and the metabolic syndrome," Expert Opin. Investig. Drugs, vol. 12(9), pp. 1489-1500 (2003).
Mital, A., "PPARs: Nuclear Receptors for Antidiabetics," CRIPS, vol. 3(1), pp. 5-8 (Jan.-Mar. 2002).
Notice of Allowance for U.S. Appl. No. 11/917,811, dated Jan. 5, 2011.
Park, Diabetes Research and Clinical Practice 66S (2004), S33-S35.
Pending Claims for U.S. Appl. No. 12/282,244, dated Jan. 25, 2011.
Pending Claims for U.S. Appl. No. 12/958,237, dated Dec. 1, 2010.
Peters et al., Biochimica et Biophysica Acta 2009, 1796, 230-241.
Sauerberg et al., Identification and Synthesis of a Novel Selective Partial PPAR-delta Agonist with Full Efficacy on Lipid Metabolism In Vitro and In Vivo J. Med. Chem., vol. 50, pp. 1495-1503 (2007).
Tiikkainen, M., et al., "Effects of Rosiglitazone and Metformin on Liver Fat Content, Hepatic Insulin Resistance, Insulin Clearance, and Gene Expression in Adipose Tissue in Patients with Type 2 Diabetes," Diabetes, vol. 53, pp. 2169-2176 (Aug. 2004).
Torra, I., et al., "Peroxisome proliferator-activated receptors: from transcriptional control to clinical practice," Curr. Opin. Lipidol., vol. 12, p. 245-254 (2001).
Vamecq, J. and Latruffe, N., "Medical significance of peroxisome proliferator-activated receptors," The Lancet, vol. 354, pp. 141-148 (Jul. 10, 1999).
Wahli, W., "Peroxisome Proliferator-Activated Receptors (PPARs): from metabolic control to epidermal wound healing," Swiss Med. Weekly, vol. 132, pp. 83-91 (2002).
Wilson et al., "The PPARs: From Orphan Receptors to Drug Discovery" J. Med. Chem., vol. 43(4), pp. 527-550 (2000).

* cited by examiner

COMPOUNDS, THEIR PREPARATION AND USE

CROSS-REFERENCE TO RELATED APPLICATIONS

This application is a 35 U.S.C. § 371 National Stage application of International Application PCT/EP2005/052014, filed May 3, 2005, which claimed priority of Danish Patent Application No. PA 2004 00719, filed May 5, 2004; this application claims priority under 35 U.S.C. § 119(e) of U.S. Provisional Application 60/570,624, filed May 13, 2004.

FIELD OF THE INVENTION

The present invention relates to novel compounds, to the use of these compounds as pharmaceutical compositions, to pharmaceutical compositions comprising the compounds and to a method of treatment employing these compounds and compositions. More specifically, the compounds of the invention can be utilised in the treatment and/or prevention of conditions mediated by the Peroxisome Proliferator-Activated Receptors (PPAR), in particular the PPARδ subtype.

BACKGROUND OF THE INVENTION

Coronary artery disease-(CAD) is the major cause of death in Type 2 diabetic and metabolic syndrome patients (i.e. patients that fall within the 'deadly quartet' category of impaired glucose tolerance, insulin resistance, hypertriglyceridemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. Studies on the molecular actions of these compounds indicate that thiazolidinediones and fibrates exert their action by activating distinct transcription factors of toe peroxisome proliferator activated receptor (PPAR) family, resulting in increased and decreased expression of specific enzymes and apolipoproteins respectively, both key-layers in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., j. Biol. Chem., 1999, Vol 274, pp. 6718-6725). Later it has been shown that PPARδ activation leads to increased levels of HDL cholesterol in db/db mice (Leibowitz et al. FEBS letters 2000, 473, 333-336). Further, a PPARδ agonist when dosed to insulin-resistant middle-aged obese rhesus monkeys caused a dramatic dose-dependent rise in serum HDL cholesterol while lowering the levels of small dense LDL, fasting triglycerides and fasting insulin (Oliver et al. PNAS 2001, 98, 5306-5311). The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARα knockout mice. Muoio et al. (J. Biol. Chem. 2002, 277, 26089-26097) showed that the high levels of PPARδ in skeletal muscle can compensate for deficiency in PPARα.

Recently, two different transgenic mouse models overexpressing PPARδ in either adipose tissue (*Cell* 2003, 113, 159-170) or in muscle tissue (*FASEB J.* 2003, 17, 209-226) have both shown up-regulation of genes (LPL, FABP, FAT, CD36, CPT1b, and ACS) and proteins (UCP-2) responsible for lipid uptake and metabolism and energy uncoupling. Both types of mice had reduced adipose tissue and were protected against high fat diet induced body weight gain. Further, pharmacological treatment of both high fat diet induced Insulin resistant mice and diabetic ob/ob with the potent PPARδ agonist GW501516 showed lowering of plasma glucose and insulin and improved insulin sensitivity (*PNAS* 2003, 100, 15924-15929). In vivo increased oxygen consumption suggesting fuel-switch from glucose to FFA, as well as FFA oxidation In skeletal muscle was demonstrated both in vivo and in vitro. Supportive for the hypothesis of skeletal muscle being the major target organ were two publications on in vitro treatment of C2C12 muscle cells with GW501516 showing regulation of genes involved with TG hydrolysis and FFA oxidation (LPL†, ACS4†, CTP1†), preferential lipid utilization (PD K4†), energy expenditure (UCP1\, -2\, -3\) and lipid efflux (ABCA1/G1\) (*BioChem. Biophys. Acta* 2003, 1633, 43-50; *Mol. Endocrin.* 2003, 17, 2477-2493). Direct and an indirect mechanisms recently demonstrated prompted the authors to suggest that "PPARδ and its ligands may serve as therapeutic targets to attenuate inflammation and slow the progression of atherosclerosis" (*Science* 2003, 302, 453-457).

Taken together these observations suggest that PPARδ activation is useful in the treatment and prevention of cardiovascular diseases and conditions including atherosclerosis, hypertriglyceridemia, and mixed dyslipidaemia as well as type 2 diabetes.

A number of PPARδ compounds have been reported to be useful in the treatment of hyperglycemia, hyperlipidemia and hypercholesterolaemia (WO 01/00603, WO 02/59098, WO 03/084916, WO 03/074050, WO 03/074051, WO 03/074052, WO 03/035603, WO 03/97607, WO 04/005253, WO 03/33493, WO 03/16291, WO 02/76957, 02/46154, WO 03/16265, WO 02/100812, WO 02/98840, WO 02/80899, WO 02/79162, WO03/072100, WO 01/25181, WO 02/14291, WO 01/79197, WO 99/4815, WO 97/28149, WO 98/27974, WO 97/28115, WO 97/27857, WO 97/28137, WO 97/27847).

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

DEFINITIONS

In the structural formulas given herein and throughout the present specification the following terms have the indicated meaning:

The term "$C_{1-6}$-alkyl" as used herein, alone or in combination, represent a linear or branched, saturated hydrocarbon chain having the indicated number of carbon atoms. Representative examples include, but are not limited to methyl, ethyl, n-propyl, isopropyl, butyl, isobutyl, sec-butyl, tert-butyl, pentyl, isopentyl, hexyl, isohexyl and the like.

The term "$C_{1-6}$-alkylcarbonyl as used herein, represents a "$C_{1-6}$-alkyl" group as defined above having the indicated number of carbon atoms linked through a carbonyl group. Representative examples include, but are not limited to, methylcarbonyl, ethylcarbonyl, n-propylcarbonyl, isopropylcarbonyl, butylcarbonyl, isobutylcarbonyl, sec-butylcarbonyl, tertbutylcarbonyl, n-pentylcarbonyl, isopentylcarbonyl, neopentylcarbonyl, tert-pentylcarbonyl, n-hexylcarbonyl, iso-hexylcarbonyl and the like.

The term "$C_{1-6}$-alkylsulfonyl" as used herein refers to a monovalent substituent comprising a "$C_{1-6}$-alkyl" group as defined above linked through a sulfonyl group. Representative examples include, but are not limited to, methylsulfonyl, ethylsulfonyl, n propylsulfonyl, isopropylsulfonyl, n-butylsulfonyl, isobutylsulfonyl, sec-butylsulfonyl, tert-butylsulfonyl, n pentylsulfonyl, isopentylsulfonyl, neopentylsulfonyl, tert-pentylsulfonyl, n-hexylsulfonyl, isohexylsulfonyl and the like.

The term "$C_{1-6}$-alkylamido" as used herein, refers to an acyl group linked through an amino group; Representative examples include, but are not limited to acetylamino, propionylamino, butyrylamino, isobutyrylamino, pivaloylamino, valerylamino and the like.

The term "C-cycloalkyl" as used herein, alone or in combination, represent a saturated monocyclic hydrocarbon group having the indicated number of carbon atoms. Representative examples include, but are not limited to cyclopropyl, cyclobutyl, cyclopentyl, cyclohexyl and the like.

The term "alkenyl" as used herein, represent an olefinically unsaturated branched or straight hydrocarbon group having from 2 to the specified number of carbon atoms and at least one double bond. Representative examples include, but are not limited to, vinyl, 1-propenyl, 2-propenyl, allyl, iso-propenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Representative examples include, but are not limited to, 1-propynyl, 2-propynyl, 1-butynyl, 2-butynyl, 1-pentynyl, 2-pentynyl and the like.

The term "$C_{4-6}$-alkenynyl" as used herein, represent an unsaturated branched or straight hydrocarbon group having from 4 to the specified number of carbon atoms and both at least one double bond and at least one triple bond. Representative examples include, but are not limited to, 1-penten-4-ynyl, 3-penten-1-ynyl, 1,3-hexadiene-5-ynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a "$C_{1-6}$-alkyl" group as defined above linked through a divalent sulfur atom having its free valence bond from the sulfur atom and having 1 to 6 carbon atoms. Representative examples include, but are not limited to, methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Examples of cycloalkoxy groups are cyclopropylthio, cyclobutylthio, cyclopentylthio, cyclohexylthio and the like.

The term "$C_{1-6}$-alkylamino" as used herein, alone or in combination, refers to a straight or branched monovalent substituent comprising a "$C_{1-6}$-alkyl" group as defined above linked through amino having a free valence bond from the nitrogen atom. Representative examples include, but are not limited to, methylamino, ethylamino, propylamino, butylamino, pentylamino and the like.

The term "$C_{1-6}$-alkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom. Representative examples include, but are not limited to, cyclopropylamino, cyclobutylamino, cyclopentylamino, cyclohexylamino and the like.

The term "$C_{1-6}$-alkoxy$C_{1-6}$-alkyl" as used herein, alone or in combination, refers to a "$C_{1-6}$-alkyl" group as defined above whereto is attached a "$C_{1-6}$-alkoxy" group as defined above. Representative examples include, but are not limited to, methoxymethyl, ethoxymethyl, methoxyethyl, ethoxyethyl and the like.

The term "aryl" as used herein refers to an aromatic monocyclic or an aromatic fused bi- or tricyclic hydrocarbon group. Representative examples include, but are not limited to, phenyl, naphthyl, anthracenyl, phenanthrenyl, azulenyl, fluorenyl, indenyl, pentalenyl and the like.

The term "arylene" as used herein refers to divalent aromatic monocyclic or a divalent aromatic fused bi- or tricyclic hydrocarbon group. Representative examples include, but are not limited to, phenylene, naphthylene and the like.

The term "arylcarbonyl" as used herein represents an "aryl" group as defined above linked through a carbonyl group. Representative examples include, but are not limited to, phenylcarbonyl, naphthylcarbonyl, anthracenylcarbonyl, phenanthrenylcarbonyl, azulenylcarbonyl and the like.

The term "arylsulfonyl" as used herein refers to an "aryl" group as defined above linked through a sulfonyl group. Representative examples include, but are not limited to, phenylsulfonyl, naphthylsulfonyl, anthracenylsulfonyl, phenanthrenylsulfonyl, azulenylsulfonyl, and the like.

The term "arylamido" as used herein refers to an arylcarbonyl group linked through an amino group. Representative examples include, but are not limited to phenylcarbonylamino, naphthylcarbonylamino, anthracenylcarbonylamino, phenanthrenylcarbonylamino, azulenylcarbonylamino and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms. Representative examples include, but are not limited to, dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a "$C_{1-6}$-alkyl" group as defined above linked through a carbonyl group. Representative examples include, but are not limited to, acetyl, propionyl, butyryl, isobutyryl, pivaloyl, valeryl and the like.

The term "heteroaryl" as used herein, alone or in combination, refers to a monovalent substituent comprising a 5-7 membered monocyclic aromatic system or a 8-10 membered bicyclic aromatic system containing one or more heteroatoms selected from nitrogen, oxygen and sulfur, e.g. furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinyl, isoindolyl, indolyl, benzimidazolyl, benzoxazolyl, benzothiazolyl, benzofuranyl, tetrazolyl, carbazolyl, benzothienyl, pteridinyl and purinyl and the like.

The term "heteroarylene" as used herein, alone or in combination, refers to divalent 5-7 membered monocyclic aromatic system or a 8-10 membered bicyclic aromatic system containing one or more heteroatoms selected from nitrogen, oxygen and sulfur, e.g. furylene, thienylene, pyrrolylene, imidazolylene, pyrazolylene, triazolylene, pyridylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinylene, indolylene, benzimidazolylene, benzofuranylene, benzothienylene, pteridinylene and purinylene and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltioxy, benzimidazolyloxy, benzofuranyloxy, pteridinyloxy and purinyloxy and the like.

The term "aralkyl" as used herein refers to a straight or branched saturated carbon chain containing from 1 to 6 carbons substituted with an aromatic carbohydride. Representative examples include, but are not limited to, benzyl, phenethyl, 3-phenylpropyl, 1-naphthylmethyl, 2-(1-naphthyl)ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom. Representative examples include, but are not limited to, (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy. Representative examples include, but are not limited to, phenylthio, (4-methylphenyl)-thio, (2-chlorophenyl)thio and the like.

The term "heterocyclyl" as used herein represents a saturated 3 to 12 membered monocyclic ring containing one or more heteroatoms selected from nitrogen, oxygen, sulfur, $S(=O)$ and $S(=O)_2$. Representative examples are aziridinyl, azetidinyl, oxetanyl, pyrrolidinyl, imidazolidinyl, oxazolidinyl, thiazolidinyl, isothiazolidinyl, piperidinyl, homopiperidinyl, piperazinyl, morpholinyl, thiomorpholinyl, 1-oxo-thiomorpholinyl, 1,1-dioxo-thiomorpholinyl, tetrahydrofuranyl, tetrahydrothienyl, tetrahydro-1,1-dioxothienyl, tetrahydropyranyl, tetrahydrothiopyranyl, 1,4-dioxanyl, 1,3-dioxanyl, and the like. Heterocyclyl is also intended to represent a saturated bicyclic ring containing one or more heteroatoms selected from nitrogen, oxygen, sulfur, S(=O) and S(=O)$_2$. Representative examples are octahydroindolyl, decahydroquinoxalinyl, and the like. Heterocyclyl is also intended to represent a saturated heterocyclic ring containing one or more heteroatoms selected from nitrogen, oxygen, sulfur, S(=O) and S(=O)$_2$ and having one or two bridges. Representative examples are 3-azabicyclo[3.2.2]nonyl, 2-azabicyclo[2.2.1]heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, and the like. Heterocyclyl is also intended to represent a saturated heterocyclic ring containing one or more heteroatoms selected from nitrogen, oxygen, sulfur, S(=O) and S(=O)$_2$ and containing one or more Spiro atoms. Representative examples are 1,4-dioxaspiro[4.5]decanyl, 8-azaspiro[4.5]decanyl, 2,8-diazaspiro[4.5]decanyl, and the like.

The term "five to eight member ring" as used herein refers to a saturated or unsaturated, substituted or unsubstituted hydrocarbon chain or hydrocarbon-heteroatom chain having from 3 to 6 atoms together with the carbon atom in Ar, to which they are attached, and the adjacent carbon atom form a five to eight member ring.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

The term "pharmaceutically acceptable" is defined as being suitable for administration to humans without adverse events.

DESCRIPTION OF THE INVENTION

The present invention relates to compounds of the general formula (I):

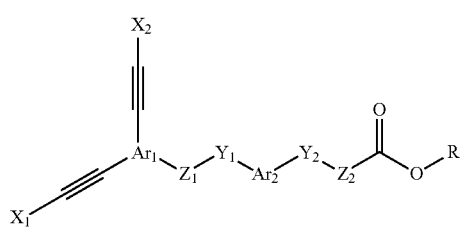

(I)

wherein $X_1$ is aryl or heteroaryl each of which is optionally substituted with one or more substituents selected from
 halogen, hydroxy, cyano, amino or carboxy; or
 $C_{1-6}$-alkyl, $C_{3-8}$-cycloalkyl, $C_{2-6}$-alkenyl, $C_{2-6}$-alkynyl, aralkyl, heteroaralkyl, $C_{1-6}$-alkoxy, $C_{3-8}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-alkylamino or $C_{3-6}$-cycloalkylamino each of which is optionally substituted with one or more of halogen or hydroxy; and $X_2$ is aryl or heteroaryl each of which is optionally substituted with one or more substituents selected from
 halogen, hydroxy, cyano, amino or carboxy; or
 $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more of halogen or hydroxy; and $Ar_1$ is arylene or heteroarylene; and
$Ar_2$ is arylene which is optionally substituted with one or more substituents selected from
 halogen, hydroxy or cyano; or
 $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{1-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or
 two of the substituents when placed in adjacent positions together with the atoms to which they are attached may form a five to eight member ring; and
$Y_1$ is O or S; and
$Y_2$ is O or S; and
$Z_1$ is —$(CH_2)_n$— wherein n is 0, 1, or 2; and
$Z_2$ is —$(CH_2)_m$— wherein m is 1, 2 or 3; and
R is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or
a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein $X_1$ is aryl optionally substituted with one or more substituents selected from
 halogen; or
 $C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_1$ is aryl optionally substituted with one or more substituents selected from
 halogen; or
 $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is aryl optionally substituted with one or more substituents selected from
 halogen; or
 $C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_1$ is aryl optionally substituted with one or more substituents selected from
halogen; or
$C_{1-6}$-alkyl or $C_{1-6}$-alkoxy, each of which is optionally substituted with one or more of halogen or hydroxy.

In another embodiment, the present invention is concerned with compounds of formula (I) wherein $X_1$ is aryl optionally substituted with one or more substituents selected from
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is aryl optionally substituted with one or more substituents selected from
halogen; or
$C_{1-6}$-alkyl or $C_{1-6}$-alkoxy, each of which is optionally substituted with one or more of hydroxy.

In another embodiment, the present invention is concerned with compounds of formula (I) wherein $X_1$ is aryl optionally substituted with one or more halogens.

In another embodiment, the present invention is concerned with compounds of formula (I) wherein $X_1$ is aryl optionally substituted with one or more of $C_{1-6}$-alkyl which is optionally substituted with one or more of halogen or hydroxy.

In another embodiment, the present invention is concerned with compounds of formula (I) wherein $X_1$ is aryl optionally substituted with one or more of $C_{1-6}$-alkyl which is optionally substituted with one or more halogens.

In another embodiment, the present invention is concerned with compounds of formula (I) wherein $X_1$ is aryl optionally substituted with one or more of $C_{1-6}$-alkyl which is optionally substituted with one or more of hydroxy.

In another embodiment, the present invention is concerned with compounds of formula (I) wherein $X_1$ is aryl optionally substituted with one or more of $C_{1-6}$-alkoxy, which is optionally substituted with one or more halogens.

In another embodiment, the present invention is concerned with compounds of formula (I) wherein $X_1$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_1$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_1$ is phenyl optionally substituted with one or more substituents selected from
halogen; or
$C_{1-6}$-alkyl or $C_{1-6}$-alkoxy, each of which is optionally substituted with one or more of halogen or hydroxy.

In another embodiment, the present invention is concerned with compounds of formula (I) wherein $X_1$ is phenyl optionally substituted with one or more substituents selected from
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is phenyl optionally substituted with one or more substituents selected from
halogen; or
$C_{1-6}$-alkyl or $C_{1-6}$-alkoxy, each of which is optionally substituted with one or more of hydroxy.

In another embodiment, the present invention is concerned with compounds of formula (I) wherein $X_1$ is phenyl optionally substituted with one or more halogens.

In another embodiment, the present invention is concerned with compounds of formula (I) wherein $X_1$ is phenyl optionally substituted with one or more of $C_{1-6}$-alkyl which is optionally substituted with one or more of halogen or hydroxy.

In another embodiment, the present invention is concerned with compounds of formula (I) wherein $X_1$ is phenyl optionally substituted with one or more of $C_{1-6}$-alkyl which is optionally substituted with one or more halogens.

In another embodiment, the present invention is concerned with compounds of formula (I) wherein $X_1$ is phenyl optionally substituted with one or more of $C_{1-6}$-alkyl which is optionally substituted with one or more hydroxy.

In another embodiment, the present invention is concerned with compounds of formula (I) wherein $X_1$ is phenyl optionally substituted with one or more of methyl or ethyl.

In another embodiment, the present invention is concerned with compounds of formula (I) wherein $X_1$ is phenyl optionally substituted with one or more of perhalomethyl.

In another embodiment, the present invention is concerned with compounds of formula (I) wherein $X_1$ is phenyl optionally substituted with one or more of hydroxymethyl.

In another embodiment, the present invention is concerned with compounds of formula (I) wherein $X_1$ is phenyl optionally substituted with one or more of $C_{1-6}$-alkoxy, which is optionally substituted with one or more halogens.

In another embodiment, the present invention is concerned with compounds of formula (I) wherein $X_1$ is phenyl optionally substituted with one or more of methoxy or ethoxy, each of which is optionally substituted with one or more halogens.

In another embodiment, the present invention is concerned with compounds of formula (I) wherein $X_1$ is phenyl optionally substituted with one or more methoxy.

In another embodiment, the present invention is concerned with compounds of formula (I) wherein $X_1$ is phenyl.

In another embodiment, the present invention is concerned with compounds of formula (I) wherein $X_1$ is heteroaryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_1$ is heteroaryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is heteroaryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_1$ is heteroaryl optionally substituted with one or more substituents selected from
halogen; or
$C_{1-6}$-alkyl or $C_{1-6}$-alkoxy, each of which is optionally substituted with one or more of halogen or hydroxy.

In another embodiment, the present invention is concerned with compounds of formula (I) wherein $X_1$ is heteroaryl optionally substituted with one or more substituents selected from
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is heteroaryl optionally substituted with one or more substituents-selected from
halogen; or
$C_{1-6}$-alkyl or $C_{1-6}$-alkoxy, each of which is optionally substituted with one or more of hydroxy.

In another embodiment, the present invention is concerned with compounds of formula (I) wherein $X_1$ is heteroaryl optionally substituted with one or more halogens.

In another embodiment, the present invention is concerned with compounds of formula (I) wherein $X_1$ is heteroaryl optionally substituted with one or more of $C_{1-6}$-alkyl which is optionally substituted with one or more of halogen or hydroxy.

In another embodiment, the present invention is concerned with compounds of formula (I) wherein $X_1$ is heteroaryl optionally substituted with one or more of $C_{1-6}$-alkyl which is optionally substituted with one or more halogens.

In another embodiment, the present invention is concerned with compounds of formula (I) wherein $X_1$ is heteroaryl optionally substituted with one or more of $C_{1-6}$-alkyl which is optionally substituted with one or more of hydroxy.

In another embodiment, the present invention is concerned with compounds of formula (I) wherein $X_1$ is heteroaryl optionally substituted with one or more of $C_{1-6}$-alkoxy, which is optionally substituted with one or more halogens.

In another embodiment, the present invention is concerned with compounds of formula (I) wherein $X_1$ is furyl or thienyl optionally substituted with one or more halogens.

In another embodiment, the present invention is concerned with compounds of formula (I) wherein $X_1$ is thienyl optionally substituted with one or more halogens.

In another embodiment, the present invention is concerned with compounds of formula (I) wherein $X_1$ is benzothienyl or benzofuryl optionally substituted with one or more of $C_{1-6}$-alkyl.

In another embodiment, the present invention is concerned with compounds of formula (I) wherein $X_1$ is pyridyl, thiazolyl or pyrrolyl, each of which is optionally substituted with one or more substituents selected from:
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is pyridyl optionally substituted with one or more substituents selected from:
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is thiazolyl optionally substituted with one or more substituents selected from:
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is pyrrolyl optionally substituted with one or more substituents selected from:
halogen; or
$C_{1-6}$-alkyl or $C_{1-6}$-alkoxy, each of which is optionally substituted with one or more halogens.

In another embodiment, the present invention is concerned with compounds of formula (I) wherein $X_1$ is pyridyl, thiazolyl or pyrrolyl, each of which is optionally substituted with one or more halogens.

In another embodiment, the present invention is concerned with compounds of formula (I) wherein $X_1$ is pyridyl optionally substituted with one or more halogens.

In another embodiment, the present invention is concerned with compounds of formula (I) wherein $X_1$ is thiazolyl optionally substituted with one or more halogens.

In another embodiment, the present invention is concerned with compounds of formula (I) wherein $X_1$ is pyrrolyl optionally substituted with one or more halogens.

In another embodiment, the present invention is concerned with compounds of formula (I) wherein $X_1$ is pyridyl, thiazolyl or pyrrolyl, each of which is optionally substituted with one or more of $C_{1-6}$-alkyl which is optionally substituted with one or more halogens.

In another embodiment, the present invention is concerned with compounds of formula (I) wherein $X_1$ is pyridyl optionally substituted with one or more of $C_{1-6}$-alkyl which is optionally substituted with one or more halogens.

In another embodiment, the present invention is concerned with compounds of formula (I) wherein $X_1$ is thiazolyl optionally substituted with one or more of $C_{1-6}$-alkyl which is optionally substituted with one or more halogens.

In another embodiment, the present invention is concerned with compounds of formula (I) wherein $X_1$ is pyrrolyl optionally substituted with one or more of $C_{1-6}$-alkyl which is optionally substituted with one or more halogens.

In another embodiment, the present invention is concerned with compounds of formula (I) wherein $X_1$ is pyridyl, thiazolyl or pyrrolyl, each of which is optionally substituted with one or more of $C_{1-6}$-alkoxy which is optionally substituted with one or more halogens.

In another embodiment, the present invention is concerned with compounds of formula (I) wherein $X_1$ is pyridyl optionally substituted with one or more of $C_{1-6}$-alkoxy which is optionally substituted with one or more halogens.

In another embodiment, the present invention is concerned with compounds of formula (I) wherein $X_1$ is thiazolyl optionally substituted with one or more of $C_{1-6}$-alkoxy which is optionally substituted with one or more halogens.

In another embodiment, the present invention is concerned with compounds of formula (I) wherein $X_1$ is pyrrolyl optionally substituted with one or more of $C_{1-6}$-alkoxy which is optionally substituted with one or more halogens.

In another embodiment, the present invention is concerned with compounds of formula (I) wherein $X_1$ is pyridyl.

In another embodiment, the present invention is concerned with compounds of formula (I) wherein $X_1$ is thiazolyl.

In another embodiment, the present invention is concerned with compounds of formula (I) wherein $X_1$ is pyrrolyl.

In another embodiment, the present invention is concerned with compounds of formula (I) wherein $X_1$ is pyrrolyl optionally substituted with $C_{1-6}$-alkyl.

In another embodiment, the present invention is concerned with compounds of formula (I) wherein $X_2$ is aryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_2$ is aryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is aryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_2$ is aryl optionally substituted with one or more substituents selected from
halogen; or
$C_{1-6}$-alkyl or $C_{1-6}$-alkoxy, each of which is optionally substituted with one or more of halogen or hydroxy.

In another embodiment, the present invention is concerned with compounds of formula (I) wherein $X_2$ is aryl optionally substituted with one or more substituents selected from
halogen; or
$C_{1-6}$-alkyl or $C_{1-6}$-alkoxy, each of which is optionally substituted with one or more halogens.

In another embodiment, the present invention is concerned with compounds of formula (I) wherein $X_2$ is aryl optionally substituted with one or more substituents selected from
halogen; or
$C_{1-6}$-alkyl or $C_{1-6}$-alkoxy, each of which is optionally substituted with one or more of hydroxy.

In another embodiment, the present invention is concerned with compounds of formula (I) wherein $X_2$ is aryl optionally substituted with one or more halogens.

In another embodiment, the present invention is concerned with compounds of formula (I) wherein $X_2$ is aryl optionally substituted with one or more of $C_{1-6}$-alkyl which is optionally substituted with one or more of halogen or hydroxy.

In another embodiment, the present invention is concerned with compounds of formula (I) wherein $X_2$ is aryl optionally substituted with one or more of $C_{1-6}$-alkyl which is optionally substituted with one or more halogens.

In another embodiment, the present invention is concerned with compounds of formula (I) wherein $X_2$ is aryl optionally substituted with one or more of $C_{1-6}$-alkyl which is optionally substituted with one or more of hydroxy.

In another embodiment, the present invention is concerned with compounds of formula (I) wherein $X_2$ is aryl optionally substituted with one or more of $C_{1-6}$-alkoxy, which is optionally substituted with one or more halogens.

In another embodiment, the present invention is concerned with compounds of formula (I) wherein $X_2$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_2$ is phenyl optionally substituted with one or more substituents selected from
halogen; or $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_2$ is phenyl optionally substituted with one or more substituents selected from
halogen; or
$C_{1-6}$-alkyl or $C_{1-6}$-alkoxy, each of which is optionally substituted with one or more of halogen or hydroxy.

In another embodiment, the present invention is concerned with compounds of formula (I) wherein $X_2$ is phenyl optionally substituted with one or more substituents selected from
halogen; or
$C_{1-6}$-alkyl or $C_{1-6}$-alkoxy, each of which is optionally substituted with one or more halogens.

In another embodiment, the present invention is concerned with compounds of formula (I) wherein $X_2$ is phenyl optionally substituted with one or more substituents selected from
halogen; or
$C_{1-6}$-alkyl or $C_{1-6}$-alkoxy, each of which is optionally substituted with one or more of hydroxy.

In another embodiment, the present invention is concerned with compounds of formula (I) wherein $X_2$ is phenyl optionally substituted with one or more halogens.

In another embodiment, the present invention is concerned with compounds of formula (I) wherein $X_2$ is phenyl optionally substituted with one or more of $C_{1-6}$-alkyl, which is optionally substituted with one or more of halogen or hydroxy.

In another embodiment, the present invention is concerned with compounds of formula (I) wherein $X_2$ is phenyl optionally substituted with one or more of $C_{1-6}$-alkyl, which is optionally substituted with one or more halogens.

In another embodiment, the present invention is concerned with compounds of formula (I) wherein $X_2$ is phenyl optionally substituted with one or more of $C_{1-6}$-alkyl, which is optionally substituted with one or more of hydroxy.

In another embodiment, the present invention is concerned with compounds of formula (I) wherein $X_2$ is phenyl optionally substituted with one or more of methyl or ethyl.

In another embodiment, the present invention is concerned with compounds of formula (I) wherein $X_2$ is phenyl optionally substituted with one or more of perhalomethyl.

In another embodiment, the present invention is concerned with compounds of formula (I) wherein $X_2$ is phenyl optionally substituted with one or more of hydroxymethyl.

In another embodiment, the present invention is concerned with compounds of formula (I) wherein $X_2$ is phenyl optionally substituted with one or more of $C_{1-6}$-alkoxy, which is optionally substituted with one or more halogens.

In another embodiment, the present invention is concerned with compounds of formula (I) wherein $X_2$ is phenyl optionally substituted with one or more of methoxy or ethoxy, each of which is optionally substituted with one or more halogens.

In another embodiment, the present invention is concerned with compounds of formula (I) wherein $X_2$ is phenyl optionally substituted with one or more methoxy.

In another embodiment, the present invention is concerned with compounds of formula (I) wherein $X_2$ is phenyl.

In another embodiment, the present invention is concerned with compounds of formula (I) wherein $X_2$ is heteroaryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more of halogen or hydroxy.

In another embodiment, the present invention is concerned with compounds of formula (I) wherein $X_2$ is heteroaryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is heteroaryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more of hydroxy.

In another embodiment, the present invention is concerned with compounds of formula (I) wherein $X_2$ is heteroaryl optionally substituted with one or more substituents selected from
  halogen; or
  $C_{1-6}$-alkyl or $C_{1-6}$-alkoxy, each of which is optionally substituted with one or more of halogen or hydroxy.

In another embodiment, the present invention is concerned with compounds of formula (I) wherein $X_2$ is heteroaryl optionally substituted with one or more substituents selected from
  halogen; or
  $C_{1-6}$-alkyl or $C_{1-6}$-alkoxy, each of which is optionally substituted with one or more halogens.

In another embodiment, the present invention is concerned with compounds of formula (I) wherein $X_2$ is heteroaryl optionally substituted with one or more substituents selected from
  halogen; or
  $C_{1-6}$-alkyl or $C_{1-6}$-alkoxy, each of which is optionally substituted with one or more of hydroxy.

In another embodiment, the present invention is concerned with compounds of formula (I) wherein $X_2$ is heteroaryl optionally substituted with one or more halogens.

In another embodiment, the present invention is concerned with compounds of formula (I) wherein $X_2$ is heteroaryl optionally substituted with one or more of $C_{1-6}$-alkyl, which is optionally substituted with one or more of halogen or hydroxy.

In another embodiment, the present invention is concerned with compounds of formula (I) wherein $X_2$ is heteroaryl optionally substituted with one or more of $C_{1-6}$-alkyl, which is optionally substituted with one or more halogens.

In another embodiment, the present invention is concerned with compounds of formula (I) wherein $X_2$ is heteroaryl optionally substituted with one or more of $C_{1-6}$-alkyl, which is optionally substituted with one or more of hydroxy.

In another embodiment, the present invention is concerned with compounds of formula (I) wherein $X_2$ is heteroaryl optionally substituted with one or more of $C_{1-6}$-alkoxy, which is optionally substituted with one or more halogens.

In another embodiment, the present invention is concerned with compounds of formula (I) wherein $X_2$ is furyl or thienyl optionally substituted with one or more halogens.

In another embodiment, the present invention is concerned with compounds of formula (I) wherein $X_2$ is thienyl optionally substituted with one or more halogens.

In another embodiment, the present invention is concerned with compounds of formula (I) wherein $X_2$ is benzothienyl or benzofuryl optionally substituted with one or more of $C_{1-6}$-alkyl.

In another embodiment, the present invention is concerned with compounds of formula (I) wherein $X_2$ is pyridyl, thiazolyl or pyrrolyl, each of which is optionally substituted with one or more substituents selected from:
  halogen; or
  $C_{1-6}$-alkyl or $C_{1-6}$-alkoxy, each of which is optionally substituted with one or more halogens.

In another embodiment, the present invention is concerned with compounds of formula (I) wherein $X_2$ is pyridyl optionally substituted with one or more substituents selected from:
  halogen; or
  $C_{1-6}$-alkyl or $C_{1-6}$-alkoxy, each of which is optionally substituted with one or more halogens.

In another embodiment, the present invention is concerned with compounds of formula (I) wherein $X_2$ is thiazolyl optionally substituted with one or more substituents selected from:
  halogen; or
  $C_{1-6}$-alkyl or $C_{1-6}$-alkoxy, each of which is optionally substituted with one or more halogens.

In another embodiment, the present invention is concerned with compounds of formula (I) wherein $X_2$ is pyrrolyl optionally substituted with one or more substituents selected from:
  halogen; or
  $C_{1-6}$-alkyl or $C_{1-6}$-alkoxy, each of which is optionally substituted with one or more halogens.

In another embodiment, the present invention is concerned with compounds of formula (I) wherein $X_2$ is pyridyl, thiazolyl or pyrrolyl, each of which is optionally substituted with one or more halogens.

In another embodiment, the present invention is concerned with compounds of formula (I) wherein $X_2$ is pyridyl optionally substituted with one or more halogens.

In another embodiment, the present invention is concerned with compounds of formula (I) wherein $X_2$ is thiazolyl optionally substituted with one or more halogens.

In another embodiment, the present invention is concerned with compounds of formula (I) wherein $X_2$ is pyrrolyl optionally substituted with one or more halogens.

In another embodiment, the present invention is concerned with compounds of formula (I) wherein $X_2$ is pyridyl, thiazolyl or pyrrolyl, each of which is optionally substituted with one or more of $C_{1-6}$-alkyl which is optionally substituted with one, or more halogens.

In another embodiment, the present invention is concerned with compounds of formula (I) wherein $X_2$ is pyridyl optionally substituted with one or more of $C_{1-6}$-alkyl which is optionally substituted with one or more halogens.

In another embodiment, the present invention is concerned with compounds of formula (I) wherein $X_2$ is thiazolyl optionally substituted with one or more of $C_{1-6}$-alkyl which is optionally substituted with one or more halogens.

In another embodiment, the present invention is concerned with compounds of formula (I) wherein $X_2$ is pyrrolyl optionally substituted with one or more of $C_{1-6}$-alkyl which is optionally substituted with one or more halogens.

In another embodiment, the present invention is concerned with compounds of formula (I) wherein $X_2$ is pyridyl, thiazolyl or pyrrolyl, each of which is optionally substituted with one or more of $C_{1-6}$-alkoxy which is optionally substituted with one or more halogens.

In another embodiment, the present invention is concerned with compounds of formula (I) wherein $X_2$ is pyridyl optionally substituted with one or more of $C_{1-6}$-alkoxy which is optionally substituted with one or more halogens.

In another embodiment, the present invention is concerned with compounds of formula (I) wherein $X_2$ is thiazolyl optionally substituted with one or more of $C_{1-6}$-alkoxy which is optionally substituted with one or more halogens.

In another embodiment, the present invention is concerned with compounds of formula (I) wherein $X_2$ is pyrrolyl optionally substituted with one or more of $C_{1-6}$-alkoxy which is optionally substituted with one or more halogens.

In another embodiment, the present invention is concerned with compounds of formula (I) wherein $X_2$ is pyridyl.

In another embodiment, the present invention is concerned with compounds of formula (I) wherein $X_2$ is thiazolyl.

In another embodiment, the present invention is concerned with compounds of formula (I) wherein $X_2$ is pyrrolyl.

In another embodiment, the present invention is concerned with compounds of formula (I) wherein $X_2$ is pyrrolyl optionally substituted with $C_{1-5}$-alkyl.

In another embodiment, the present invention is concerned with compounds of formula (I) wherein $Ar_1$ is phenylene.

In another embodiment, the present invention is concerned with compounds of formula (I) wherein $Ar_1$ is thienylene.

In another embodiment, the present invention is concerned with compounds of formula (I) wherein $Ar_1$ is pyridylene.

In another embodiment, the present invention is concerned with compounds of formula (I) wherein $Ar_2$ is phenylene which is optionally substituted with one or more substituents selected from
  halogen, hydroxy or cyano; or
  $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{1-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens, or
  two of the substituents when placed in adjacent positions together with the atoms to which they are attached may form a five to eight member ring.

In another embodiment, the present invention is concerned with compounds of formula (I) wherein $Ar_2$ is phenylene which is optionally substituted with one or more substituents selected from
  halogen; or
  $C_{1-6}$-alkyl, $C_{1-6}$-alkoxy, aryloxy or aralkoxy each of which is optionally substituted with one or more halogens; or
  two of the substituents when placed in adjacent positions together with the atoms to which they are attached may form a five membered carbon cycle.

In another embodiment, the present invention is concerned with compounds of formula (I) wherein $Ar_2$ is phenylene which is optionally substituted with halogen.

In another embodiment, the present invention is concerned with compounds of formula (I) wherein $Ar_2$ is phenylene which is optionally substituted with one or more of $C_{1-6}$-alkyl optionally substituted with one or more halogens.

In another embodiment, the present invention is concerned with compounds of formula (I) wherein $Ar_2$ is phenylene which is optionally substituted with one or more of $C_{1-6}$-alkoxy optionally substituted with one or more halogens.

In another embodiment, the present invention is concerned with compounds of formula (I) wherein $Ar_2$ is phenylene which is optionally substituted with one or more of aryloxy optionally substituted with one or more halogens.

In another embodiment, the present invention is concerned with compounds of formula (I) wherein $Ar_2$ is phenylene which is optionally substituted with one or more of aralkoxy optionally substituted with one or more halogens.

In another embodiment, the present invention is concerned with compounds of formula (I) wherein $Ar_2$ is phenylene which is optionally substituted with methyl.

In another embodiment, the present invention is concerned with compounds of formula (I) wherein $Ar_2$ is phenylene.

In another embodiment, the present invention is concerned with compounds of formula (I) wherein $Ar_2$ is indenylene.

In another embodiment, the present invention is concerned with compounds of formula (I) wherein $Y_1$ is S.

In another embodiment, the present invention is concerned with compounds of formula (I) wherein $Y_1$ is O.

In another embodiment, the present invention is concerned with compounds of formula (I) wherein $Y_2$ is O.

In another embodiment, the present invention is concerned with compounds of formula (I) wherein $Y_2$ is S.

In another embodiment, the present invention is concerned with compounds of formula (I) wherein n is 0 or 1.

In another embodiment, the present invention is concerned with compounds of formula (I) wherein n is O.

In another embodiment, the present invention is concerned with compounds of formula (I) wherein m is 1 or 2.

In another embodiment, the present invention is concerned with compounds of formula (I) wherein m is 1.

In another embodiment, the present invention is concerned with compounds of formula (I) wherein R is hydrogen or $C_{1-6}$-alkyl.

In another embodiment, the present invention is concerned with compounds of formula (I) wherein R is hydrogen.

In another embodiment, the present invention is concerned with compounds of formula (I) wherein R is methyl or ethyl.

In another embodiment, the present invention is concerned with compounds of formula I wherein alkyl is methyl or ethyl.

In another embodiment, the present invention is concerned with compounds of formula I wherein alkenyl is vinyl or 1-propenyl.

In another embodiment, the present invention is concerned with compounds of formula I wherein alkynyl is 1-propynyl.

In another embodiment, the present invention is concerned with compounds of formula I wherein alkenynyl is 1-pentene-4-yne.

In another embodiment, the present invention is concerned with compounds of formula I wherein alkoxy is methoxy, ethoxy, isopropoxy or cyclopropoxy.

In another embodiment, the present invention is concerned with compounds of formula I wherein aryl is phenyl.

In another embodiment, the present invention is concerned with compounds of formula I wherein arylene is phenylene.

In another embodiment, the present invention is concerned with compounds of formula I wherein halogen is bromine, fluorine or chlorine.

In another embodiment, the present invention is concerned with compounds of formula I wherein perhalomethyl is trifluoromethyl.

In another embodiment, the present invention is concerned with compounds of formula I wherein perhalomethoxy is trifluoromethoxy.

In another embodiment, the present invention is concerned with compounds of formula I wherein heteroaryl is furyl or thienyl.

In another embodiment, the present invention is concerned with compounds of formula I wherein heteroaryl is benzofuryl or benzothienyl.

In another embodiment, the present invention is concerned with compounds of formula I wherein heteroaryl is pyridyl.

In another embodiment, the present invention is concerned with compounds of formula I wherein heteroaryl is thiazolyl.

In another embodiment, the present invention is concerned with compounds of formula I wherein heteroaryl is pyrrolyl.

In another embodiment, the present invention is concerned with compounds of formula I wherein arylene is phenylene.

In another embodiment, the present invention is concerned with compounds of formula I wherein heteroarylene is thienylene.

In another embodiment, the present invention is concerned with compounds of formula I wherein heteroarylene is pyridylene.

In another embodiment, the present invention is concerned with compounds of formula I wherein aralkyl is benzyl.

In another embodiment, the present invention is concerned with compounds of formula I wherein aryloxy is phenoxy.

In another embodiment, the present invention is concerned with compounds of formula I wherein aralkoxy is benzyloxy.

In another embodiment, the present invention is concerned with compounds of formula I which are PPARδ agonists.

In another embodiment, the present invention is concerned with compounds of formula I which are selective PPARδ agonists.

Examples of specific compounds of the invention are:
{4-[3-(4-Chloro-phenylethynyl)-5-pyridin-2-ylethynyl-phenylsulfanyl]-2-methyl-phenoxy}-acetic acid;
[4-(3,5-Bis-pyridin-2-ylethynyl-phenylsulfanyl)-2-methylphenoxy]-acetic acid;
{4-[3,5-Bis-(3-methoxy-phenylethynyl)-phenylsulfanyl]-2-methyl-phenoxy}-acetic acid; or
a salt thereof with a pharmaceutically acceptable acid or base, or any optical isomer or mixture of optical isomers, including a racemic mixture, or any tautomeric forms.

Other examples of specific compounds of the invention are:
[4-[3,5-Bis-[(thiazol-2-yl)ethynyl]phenylsulfanyl]-2-methylphenoxy]acetic acid;
[4-[3,5-Bis-(3,4-dimethoxyphenylethynyl)phenylsulfanyl]-2-methylphenoxy]acetic acid;
[4-[2,6-Bis-[(4-chlorophenyl)ethynyl]pyridine-4-ylsulfanyl]-2-methylphenoxy]acetic acid;
[4-[2,6-Bis[(2-pyridyl)ethynyl]pyridine-4-ylsulfanyl]-2-methylphenoxy]acetic acid;
[2-Methyl-4-[2-(2-pyridylethynyl)-6-[4-trifluoromethylphenyl)ethynyl]pyridine-4-ylsulfanyl]-phenoxy]acetic acid;
[4-[3,5-Bis-(1-methyl-1H-pyrrol-2-ylethynyl)phenylsulfanyl]-2-methylphenoxy]acetic acid;
[2-Methyl-4-[2,6-bis[(4-trifluoromethylphenyl)ethynyl]pyridyl-4-sulfanyl]phenoxy]acetic acid;
{7-[2,6-Bis-(4-chloro-phenylethynyl)-pyridin-4-ylsulfanyl]-indan-4-yloxy}-acetic acid;
{7-[2,6-Bis-(4-hydroxymethyl-phenylethynyl)-pyridin-4-yl-sulfanyl]-indan-4-yloxy}-acetic acid;
{4-[2,6-bis-(4-hydroxymethyl-phenylethynyl)-pyridin-4-yl-sulfanyl]-2-methyl-phenoxy}-acetic acid;
{4-[2,6-bis-(2-hydroxymethyl-phenylethynyl)-pyridin-4-yl-sulfanyl]-2-methyl-phenoxy}-acetic acid;
[4-[3,5-Bis-[(4-trifluoromethylphenyl)ethynyl]benzyloxy]-2-methylphenoxy]acetic acid;
[4-[3,5-Bis[(2-thienyl)ethynyl]benzyloxy]-2-methylphenoxy]acetic acid;
[4-[4,6-Bis[(4-trifluoromethylphenyl)ethynyl]pyridin-2-yl-sulfanyl]-2-methylphenoxy]acetic acid;
{4-[2,6-Bis-(4-trifluoromethyl-phenylethynyl)-pyridin-4-ylmethylsulfanyl]-2-methyl-phenoxy}-acetic acid;
{4-[2,6-Bis-(4-trifluoromethyl-phenylethynyl)-pyridin-4-ylmethoxy]-2-methyl-phenoxy}-acetic acid;
{7-[2,6-Bis-(4-trifluoromethyl-phenylethynyl)-pyridin-4-ylmethylsulfanyl]-indan-4-yloxy}-acetic acid;
{4-[3,5-Bis-(4-chloro-phenylethynyl)-benzyloxy]-2-methyl-phenoxy}-acetic acid;
or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

In another aspect, the present invention relates to a method of treating and/or preventing Type I or Type II diabetes.

In a still further aspect, the present invention relates to the use of one or more compounds of the general formula I or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, artherosclerosis, hyperlipidemia, coronary artery disease, myocardial ischemia and other cardiovascular disorders.

In still another aspect, the present compounds are useful for the treatment and/or prophylaxis of diseases or complications related to atherosclerosis such as coronary artery diseases, coronary heart diseases, heart attack, myocardial infarct, coronary infarct, transient ischemic attack (TIA) or stroke.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

In yet another aspect, the invention also relates to the use of the present compounds, which after administration lower the bio-markers of atherosclerosis like, but not limited to, c-reactive protein (CRP), TNFα and IL-6.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an xglucosidase inhibitor eg. miglitol or acarbose.

In another embodiment the present compounds are administered in combination with an agent acting on the ATP-dependent potassium channel of the 5-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, fenofibrate, bezafibrate, tesaglitazar, EML-4156, LY-518674, LY-519818, MK-767, atorvastatin, fluvastatin lovastatin, pravastatin, simvastatin, cerivastin, acipimox, ezetimibe, probucol, dextrothyroxine or nicotinic acid.

In yet another embodiment the present compounds are administered in combination with a thiazolidinedione e.g. troglitazone, ciglitazone, pioglitazone or rosiglitazone.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tableted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

EXAMPLES

The following examples and general procedures refer to intermediate compounds and final products identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by nuclear magnetic resonance (NMR). NMR shifts (δ) are given in parts per million (ppm. Mp is melting point and is given in ° C.

The abbreviations as used in the examples have the following meaning:
THF: tetrahydrofuran
DMSO: dimethylsulfoxide
CDCl$_3$: deuterated chloroform
DMF: N,N-dimethylformamide
min: minute
h: hours General Procedure (A)
Step A:
Reacting the compound of formula II

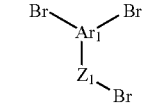

(II)

wherein $Ar_1$ and $Z_1$ are defined as above, with a compound of formula III

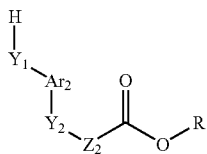
(III)

wherein $Y_1, Ar_2, Y_2, Z_2$ and R are defined as above, except that R is not hydrogen, under palladium assisted conditions (n=0), using reagents such as $PdCl_2(dppf)/Et_3N/NMP$ and the like, or alkylating conditions (n=1 and 2), using $K_2CO_3$/acetone and the like, to obtain a compound of formula IV

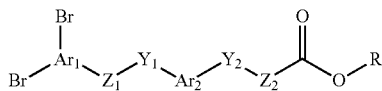
(IV)

wherein $Y_1, Y_2, Ar_1, Ar_2, Z_1, Z_2$ and R are defined as above, except that R is not hydrogen.
Step B:
Reacting an compound of formula IV, wherein $Y_1, Y_2, Ar_1, Ar_2, Z_1, Z_2$ and R are defined as above, except that R is not hydrogen, with an acetylene derivative of $X_1$ or $X_2$ under appropriate coupling conditions as $Pd_2(dba)_3/Pd(P(t-Bu)_3)_2/CuI/iPr_2NH/THF$ and the like, to give a compound of formula I, wherein $X_1, X_2, Y_1, Y_2, Ar_1, Ar_2, Z_1, Z_2$ and R are defined as above, except that R is not hydrogen.
General Procedure (B)
Step A:
Reacting the compound of formula II, wherein $Ar_1$ and $Z_1$ are defined as above, with an acetylene derivative of $X_1$ or $X_2$, wherein $X_1$ and $X_2$ are as defined above, under appropriate coupling conditions as $Pd_2(dba)_3/Pd(P(t-Bu)_3)_2/CuI/iPr_2NH/THF$ and the like, to give a compound of formula V

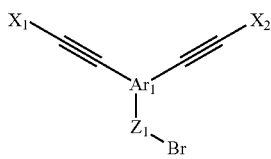
(V)

wherein $X_1, X_2, Ar_1$ and $Z_1$ are defined as above.
Step B:
Reacting the compound of formula V, wherein $X_1, X_2, Ar_1$ and $Z_1$ are defined as above, with a compound of formula II, wherein $Y_1, Ar_2, Y_2, Z_2$ and R are defined as above, except that R is not hydrogen, under palladium assisted conditions (n=0), using reagents such as $PdCl_2(dppf)/Et_3N/NMP$ and the like, or alkylating conditions (n=1 and 2), using $K_2CO_3$/acetone and the like, to obtain a compound of formula I, wherein $X_1, X_2, Y_1, Y_2, Ar_1, Ar_2, Z_1, Z_2$ and R are defined as above, except that R is not hydrogen.
General Procedure (C)
Step A:
By chemical or enzymatic saponification of a compound of formula I, wherein $X_1, X_2, Y_1, Y_2, Ar_1, Ar_2, Z_1, Z_2$ and R are defined as above, except that R is not hydrogen to give a compound of formula I, wherein $X_1, X_2, Y_1, Y_2, Ar_1, Ar_2, Z_1, Z_2$ and R are defined as above, except that R is hydrogen.

Experimental

HPLC Systems

HPLC Method A
The RP-purification was performed on a Gilson system (4 Gilson 306 pumps, Gilson 155 detector, Gilson reodyne manual injection, Gilson 811C mixer and a Gilson 202 fraction collector) using a Phenomenex RP synergi-MAX column (3 μm, 30 mm×250 mm) with gradient elution, 5% to 100% solvent B (acetonitrile) in solvent A (water) within 40 min, 60 ml/min, detection at 210 nm, temperature rt. The pooled fractions are either evaporated to dryness in vacuo, or evaporated in vacuo until the MeCN is removed, and then frozen and freeze dried.
HPLC Method B
The RP-purification was performed on a Gilson system (3 Gilson 306 pumps, Gilson 170 DAD detector and a Gilson 215 liquid-handler) using a Waters X-terra RP (10 μm, 30 mm×150 mm) with gradient elution, 5% to 95% solvent B (0.05% TFA in acetonitrile) in solvent A (0.05% TFA in water) within 15 min, 40 ml/min, detection at 210 nm, temperature rt. The pooled fractions are either evaporated to dryness in vacuo, or evaporated in vacuo until the MeCN is removed, and then frozen and freeze dried.
HPLC-MS (System 1)
The RP-analysis was performed on an Agilent HPLC system (1100 degasser, 1100 pump, 1100 injector and a 1100 DAD) fitted with an Agilent MS detector system Model VL (MW 0-1000) and a S.E.D.E.R.E Model Sedex 55 ELS detector system using a Waters X-terra MS C18 column (5 μm, 3.0 mm×50 mm) with gradient elution, 5% to 95% solvent B (0.05% TFA in acetonitrile) in solvent A (0.05% TFA in water) within 3 min, 2.7 ml/min.
TEA: Triethylamine
NMP: N-methyl-pyrolidone Example 1

[4-[3,5-Bis-(3-methoxyphenylethynyl)phenylsulfanyl]-2-methylphenoxy]acetic acid

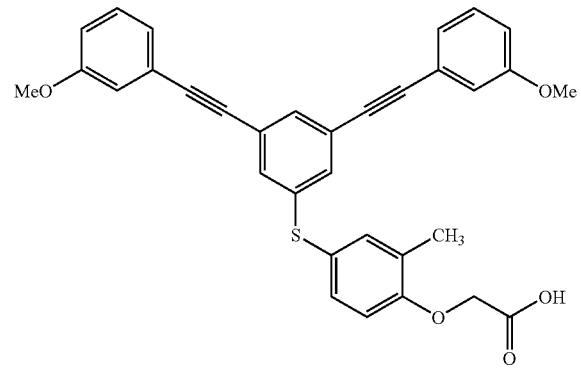

General Procedure (A)
Step A:
A mixture of ethyl (4-mercapto-2-methylphenoxy)acetic acid (1.14 g, 5.0 mmol), 1,3,5-tribromobenzene (1.88 g, 6.0 mmol), [1,1'-bis(diphenylphosphino)ferrocene]dichloropalladium complex with dichloromethane (0.205 g, 0.25 mmol), triethylamine (2.7 mL, 10 mmol) and N-methylpyrrolidin-2-one (10 mL) were heated under nitrogen at 80° C. for 4 h. The reaction mixture was then poured into water (100 mL), acidified with hydrochloric acid and extracted with ethyl acetate (3×30 mL). The combined organic layers were dried with anhydrous magnesium sulfate and evaporated in vacuo. Column chromatography of the crude product (silica gel Fluka 60, hexanes/ethyl acetate 95:5) afforded ethyl [(3,5-dibromophenylsulfanyl)-2-methylphenoxy]acetate.

Yield: 1.227 g (62%).

$R_F$ (SiO$_2$, hexanes/ethyl acetate 9:1) 0.55.

$^1$H NMR spectrum (200 MHz, CDCl$_3$, $\delta_H$): 7.48 (t, J=1.7 Hz, 1H); 7.33-7.25 (m, 2H); 7.12 (d, J=1.7 Hz, 2H); 6.72 (d, J=8.9 Hz, 1H); 4.68 (s, 2H); 4.28 (q, J=7.1 Hz, 1H); 2.30 (s, 3H); 1.31 (t, J=7.1 Hz, 3H).

Step B:

In nitrogen atmosphere, the above ester (115 mg, 0.25 mmol) and 1-ethynyl-3-methoxybenzene (97 μL, 0.75 mmol) were dissolved in anhydrous tetrahydrofuran (4 mL). 0.15 M Solution of tri-tert-butylphosphine in cyclohexane (0.2 mL, 0.03 mmol) was added via syringe. Copper(I) iodide (1.9 mg, 0.01 mmol), dichloro(bisbenzonitrile)palladium (5.7 mg, 0.015 mmol) and diisopropylamine (84 μL, 0.60 mmol) were added. The traces of the air were removed and the mixture was stirred under nitrogen at ambient temperature overnight. The mixture was diluted with ethyl acetate (10 mL) and filtered through a short path of silica gel. The filtrate was concentrated and purified by column chromatography (silica gel Fluka 60, hexanes/ethyl acetate 7:3-1:1-3:7) yielding ethyl [4-[3,5-bis-(3-methoxyphenylethynyl)-phenylsulfanyl]-2-methylphenoxy]acetate.

Yield: 87 mg (62%).

$R_F$ (SiO$_2$, hexanes/ethyl acetate 9:1) 0.25.

$^1$H NMR spectrum (200 MHz, CDCl$_3$, $\delta_H$): 7.48 (t, J=1.4 Hz, 1H); 7.35-7.25 (m, $\delta_H$); 7.15-7.01 (m, 4H); 6.95-6.85 (m, 2H); 6.72 (d, J=8.5 Hz, 1H); 4.67 (s, 2H); 4.27 (q, J=7.1 Hz, 2H); 2.30 (s, 3H); 1.29 (t, J=7.1 Hz, 3H).

General Procedure (C)

Step A:

To an ice cooled solution of the above ester (87 mg, 0.15 mmol) in a mixture tetrahydrofuran/methanol 3:1 (4 mL), a solution of lithium hydroxide monohydrate (8.4 mg, 0.2 mmol) in water (1 mL) was added. After stirring for 2 h at 0° C., water was added, the mixture was acidified with hydrochloric acid and extracted with ethyl acetate (3×20 mL). The combined organic extracts were dried with anhydrous sodium sulfate, filtered and evaporated in vacuo. The residue was purified by column chromatography (silica gel Fluka 60, dichloromethane/methanol 9:1) gave the title acid.

Yield: 65 mg (80%).

$R_F$ (SiO$_2$, dichloromethane/methanol 9:1) 0.45.

The above acid was dissolved in dichloromethane (2 mL) and solution of L-Lysine (18 mg, 0.12 mmol) in methanol/water (1:1, 5 mL) was added. The mixture was evaporated in vacuo and the residue was re-dissolved in dichloromethane (5 mL). Careful precipitation with ether at low temperature (freezer) afforded L-lysinate of the title compound.

Yield: 63 mg (62%, related to the ester).

M.p. 111-125° C. (dichloromethane/ether).

$^1$H NMR spectrum (200 MHz, AcOH-d$_4$, $\delta_H$): 7.40-6.70 (m, 14H); 4.68 (s, 2H); 3.96 (t, J=7.0 Hz, 1H); 3.70 (s, 3H); 2.98 (t, J=7.3 Hz, 2H); 2.18 (s, 3H); 1.71-1.38 (m, $\delta_H$).

Example 2

[4-[3,5-Bis-[(pyridin-2-yl)ethynyl]phenylsulfanyl]-2-methylphenoxy]acetic acid

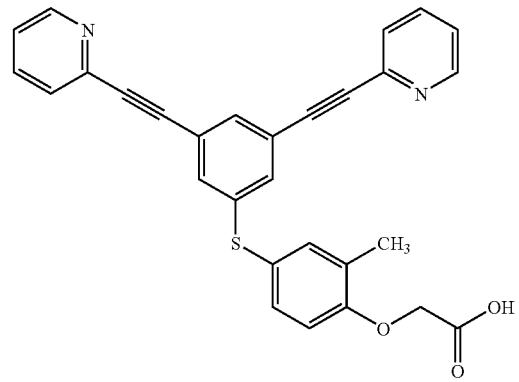

General Procedure (A)

Step B:

In nitrogen atmosphere, ethyl [4-(3,5-dibromophenylsulfanyl)-2-methylphenoxy]-acetate (138 mg, 0.30 mmol; prepared as described in example 1) and 2-ethynylpyridine (80 μL, 0.80 mmol) were dissolved in anhydrous tetrahydrofuran (4 mL). 0.15 M Solution of tri-tert-butylphosphine in cyclohexane (0.2 mL, 0.03 mmol) was added via syringe. Copper (I) iodide (1.9 mg, 0.01 mmol), dichloro(bisbenzonitrile)palladium (5.7 mg, 0.015 mmol) and diisopropylamine (112 μL, 0.80 mmol) were added. Traces of the air were removed and mixture was stirred under nitrogen at ambient temperature overnight and then at 50° C. for 1 h. The mixture was diluted with ethyl acetate (10 mL) and filtered through a short path of silica gel. The filtrate was concentrated and purified by column chromatography (silica gel Fluka 60, hexanes/ethyl acetate 7:3-1:1-3:7) yielding ethyl [4-[3,5-bis-[(pyridin-2-yl)ethynyl]-phenylsulfanyl]-2-methylphenoxy]acetate.

Yield: 97 mg (64%).

$R_F$ (SiO$_2$, hexanes/ethyl acetate 1:1) 0.30.

$^1$H NMR spectrum (200 MHz, CDCl$_3$, $\delta_H$): 8.62 (d, J=5.9 Hz, 2H); 7.74-7.64 (m, 2H); 7.58-7.48 (m, 3H); 7.35-7.22 (m, $\delta_H$); 6.72 (d, J=9.0 Hz, 1H); 4.68 (s, 2H); 4.28 (q, J=7.2 Hz, 2H); 2.30 (s, 3H); 1.28 (t, J=7.2 Hz, 3H).

General Procedure (C)

Step A:

To an ice-cooled solution of the above ester (97 mg, 0.19 mmol) in a mixture tetrahydrofuran/methanol 3:1 (4 mL), a solution of lithium hydroxide monohydrate (12 mg, 0.30 mmol) in water (1 mL) was added. After stirring for 1 h at 0° C., an aqueous solution of ammonium chloride (20 mL) was added and the mixture was extracted with ethyl acetate (3×25 mL). The combined organic extracts were dried with anhydrous sodium sulfate and evaporated in vacuo. Crude title acid was dissolved in tetrahydrofuran (5 mL) and aqueous solution of Lysine (27 mg, 0.19 mmol) was added. The mixture was evaporated to dryness and the residue was re-dissolved in tetrahydrofuran (5 mL). Careful precipitation with acetonitrile afforded L-lysinate of the title compound.

Yield: 102 mg (86%).

$R_F$ (SiO$_2$, dichloromethane/methanol 4:1) 0.45 (free acid).
M.p. 143-155° C. (tetrahydrofuran/acetonitrile).

$^1$H NMR spectrum (200 MHz, AcOH-d$_4$, $\delta_H$): 8.63 (d, J=5.1 Hz, 2H); 7.92-7.78 (m, 2H); 7.62-7.24 (m, 9H); 6.81 (d, J=9.2 Hz, 1H); 4.72 (s, 2H); 3.97 (bs, 1H); 2.99 (bs, 2H); 2.19 (s, 3H); 1.74-1.40 (m, $\delta_H$).

Example 3

[4-[3-(4-Chlorophenylethynyl)-5-[(pyridin-2-yl)ethynyl]phenylsulfanyl]-2-methylphenoxy]acetic acid

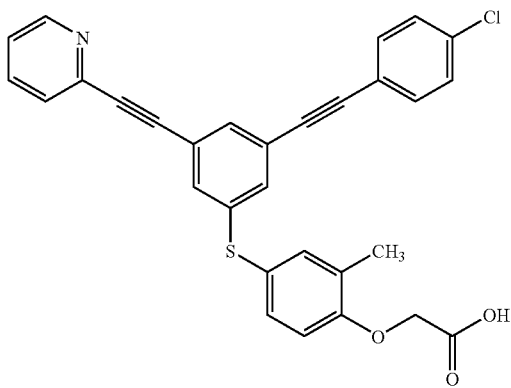

General Procedure (A)
Step B:

In nitrogen atmosphere, ethyl [4-(3,5-dibromophenylsulfanyl)-2-methylphenoxy]-acetate (460 mg, 1 mmol; prepared as described in example 1) and 2-ethynylpyridine (110 µL, 1.1 mmol) were dissolved in anhydrous tetrahydrofuran (7 mL). 0.15 M Solution of tri-tert-butylphosphine in cyclohexane (0.6 mL, 0.06 mmol) was added via syringe. Copper(I) iodide (3.8 mg, 0.02 mmol), dichloro(bisbenzonitrile)palladium (11 mg, 0.03 mmol) and diisopropylamine (155 µL, 1.1 mmol) were added. Traces of the air were removed and mixture was stirred under nitrogen at 40° C. overnight. The mixture was diluted with ethyl acetate (10 mL) and filtered through a short path of silica gel. The filtrate was concentrated and purified by column chromatography (silica gel Fluka 60, hexanes/ethyl acetate 90:10-85:15) yielding ethyl [4-[3-bromo-5-[(pyridin-2-yl)ethynyl]phenylsulfanyl]-2-methylphenoxy]acetate beside of 144 mg (30%) of unchanged starting dibromo derivative.

Yield: 254 mg (52%).
$R_F$ (SiO$_2$, hexanes/ethyl acetate 3:1) 0.40.
$^1$H NMR spectrum (200 MHz, CDCl$_3$, $\delta_H$): 8.59 (d, J=5.6 Hz, 1H); 7.68 (dt, J=1.8 and 7.7 Hz, 1H); 7.54-7.46 (m, 2H); 7.33-7.19 (m, 5H); 6.72 (d, J=9.0 Hz, 1H); 4.69 (s, 2H); 4.28 (q, J=7.2 Hz, 2H); 2.30 (s, 3H); 1.32 (t, J=7.2 Hz, 3H).

The above ester (238 mg, 0.49 mmol) and (4-chlorophenyl)acetylene (82 mg, 0.6 mmol) were dissolved in anhydrous tetrahydrofuran (5 mL) in nitrogen atmosphere. 0.15 M Solution of tri-tert-butylphosphine in cyclohexane (0.2 mL, 0.03 mmol) was added via syringe. Copper(I) iodide (2 mg, 0.01 mmol), dichloro(bisbenzonitrile)palladium (6 mg, 0.015 mmol) and diisopropylamine (70 µL, 0.5 mmol) were added. Traces of the air were removed and the mixture was stirred under nitrogen at 60° C. for 1 h. The mixture was diluted with ethyl acetate (10 mL) and filtered through a short path of silica gel. The filtrate was concentrated and purified by column chromatography (silica gel Fluka 60, hexanes/ethyl acetate 90:1-85:15). The mixture obtained mixture of the product and unreacted starting compound was separated using preparative HPLC (acetonitrile-0.1% trifluoroacetic acid in water, C-18 silica gel, Luna column—Phenomenex) yielding trifluoroacetate salt of ethyl [4-[3-(4-chlorophenylethynyl)-5-[(pyridin-2-yl)ethynyl]phenylsulfanyl]-2-methylphenoxy]acetate.

Yield: 126 mg (40%).
$R_F$ (SiO$_2$, hexanes/ethyl acetate 3:1) 0.40.
$^1$H NMR spectrum (200 MHz, CDCl$_3$, $\delta_H$): 8.86 (d, J=5.7 Hz, 1H); 8.24 (dt, J=1.6 and 7.8 Hz, 1H); 7.84 (d, J=8.2 Hz, 1H); 7.78-7.68 (m, 1H); 7.56 (t, J=1.5 Hz, 1H); 7.48-7.24 (m, 8H); 6.73 (d, J=9.1 Hz, 1H); 4.69 (s, 2H); 4.28 (q, J=7.1 Hz, 2H); 2.30 (s, 3H); 1.30 (t, J=7.0 Hz, 3H).

General Procedure (C)
Step A:

To an ice cooled solution of the above trifluoroacetate salt (105 mg, 0.19 mmol) in a mixture tetrahydrofuran/methanol 3:1 (4 mL), a solution of lithium hydroxide monohydrate (19 mg, 0.46 mmol) in water (1 mL) was added. After stirring for 1 h at 0° C., aqueous solution of ammonium chloride was added and the mixture was extracted with ethyl acetate (3×20 mL). The combined organic extracts were dried with anhydrous sodium sulfate and evaporated in vacuo. The crude product was dissolved in the mixture dichloromethane/ethanol (1:1, 5 mL) and 1 M aqueous hydrochloric acid (0.2 mL, 0.2 mmol) was added. The solid hydrochloride of the title acid was obtained by precipitation with ether.

$R_F$ (SiO$_2$, dichloromethane/methanol 9:1) 0.2 (free acid).
M.p. 185-189° C.
$^1$H NMR spectrum (200 MHz, AcOH-d$_4$, $\delta_H$): 8.60 (bs, 1H); 7.95-7.77 (m, 1H); 7.75-7.13 (m, 11H); 6.96 (d, J=8.6 Hz, 1H); 4.79 (s, 2H); 2.22 (s, 3H).

Example 4

[4-[3,5-Bis-[(thiazol-2-yl)ethynyl]phenylsulfanyl]-2-methylphenoxy]acetic acid

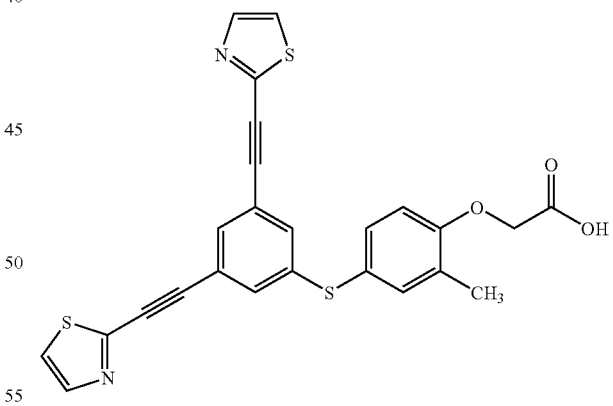

Copper(I)iodide (38 mg, 0.20 mmol), dichlorobis(triphenylphosphine)palladium(II) (250 mg, 0.40 mmol) and N,N-diisopropylamine (1.40 g, 14 mmol) were added to a solution of 2-iodothiazole (1.50 g, 7.0 mmol; prepared as described in J. Org. Chem. 1988, 53, 2489) and dry tetrahydrofuran (50 mL). The reaction mixture was degassed and trimethylsilylacetylene (1.40 g, 14 mmol) was added in two portions under nitrogen atmosphere. The reaction was heated to 50° C. for 12 h. The formed precipitate and separated palladium were removed by filtration through a short path of silica gel. The filtrate was concentrated in vacuo and the residue was purified by column chromatography (silica gel Fluka 60: hexane/ethyl acetate 98:2-90:10) yielding 2-(trimethylsilylethynyl)thiazole as yellow oil.

Yield: 600 mg (32%).

$R_F$ (SiO$_2$, hexane/ethyl acetate 90:10) 0.30.

$^1$H NMR spectrum (200 MHz, CDCl$_3$, $\delta_H$): 7.75 (d, J=3.3 Hz, 1H); 7.29 (d, J=3.3 Hz, 1H); 0.22 (bs, 9H).

General Procedure (A)
Step B:

1 M Solution of tetrabutylammonium fluoride (4.0 mL, 4.00 mmol) and absolute ethanol (5 mL) were added to a solution of 2-(trimethylsilylethynyl)thiazole (600 mg, 3.20 mmol) and ethyl [4-(3,5-dibromophenylsulfanyl)-2-methylphenoxy]acetate (460 mg, 1.00 mmol; prepared as described in example 1) in dry tetrahydrofuran (15 mL). The reaction mixture was stirred for 10 min at ambient temperature and subsequently degassed. In atmosphere of nitrogen, 0.15 M solution of tri-t-butylphosphine in cyclohexane (0.7 mL, 0.10 mmol), copper(I)iodide (8 mg, 0.04 mmol), tris(dibenzylideneacetone)dipalladium chloroform complex (103 mg, 0.05 mmol) and N,N-diisopropylamine (500 mg, 4.0 mmol) were added to the reaction mixture and the resulting mixture was heated at 50° C. for 12 h. The solution was filtered through a short path of silica gel, concentrated in vacuo and the residue was separated by column chromatography (silica gel Ruka 60: hexane/ethyl acetate 95:5-50:50) yielding mono and disubstituted product.

Ethyl [4-[3-Bromo-5-[(thiazol-2-yl)ethynyl]phenylsulfanyl]-2-methylphenoxy]acetate Yields: 140 mg (30%).

$R_F$ (SiO$_2$, hexane/ethyl acetate 90:10) 0.40.

$^1$H NMR spectrum (200 MHz, CDCl$_3$, 5H): 7.84 (d, J=2.9 Hz, 1H); 7.43 (m, 1H); 7.39 (d, J=3.1 Hz, 1H); 7.30 (m, 1H); 7.28 (m, 1H); 7.23 (m, 1H); 7.15 (m, 1H); 6.71 (d, J=9.1 Hz, 1H); 4.67 (s, 2H); 4.25 (q, J=7.2 Hz, 2H); 2.28 (s, 3H); 1.27 (t, J=7.1 Hz, 3H).

Ethyl [4-[3,5-Bis[(thiazol-2-yl)ethynyl]phenylsulfanyl]-2-methylphenoxy]acetate

Yields: 250 mg (50%).

$R_F$ (SiO$_2$, hexane/ethyl acetate 90:10) 0.15.

$^1$H NMR spectrum (200 MHz, CDCl$_3$, $\delta_H$): 7.87 (d, J=3.2 Hz, 2H); 7.55 (m, 1H); 7.41 (d, J=3.2 Hz, 2H); 7.35 (m, 1H); 7.32 (m, 2H); 7.29 (bd, J=8.6 Hz, 1H); 6.74 (d, J=9.0 Hz, 1H); 4.70 (s, 2H); 4.28 (q, J=7.1 Hz, 2H); 2.32 (s, 3H); 1.30 (t, J=7.1 Hz, 3H).

General Procedure (C)
Step A:

The above disubstituted ester (250 mg, 0.48 mmol) was dissolved in tetrahydrofuran/methanol/water mixture (5:1:1, 5 mL), saturated solution of lithium hydroxide (0.5 mL) in water was added and the resulting reaction mixture was stirred for 2 h at ambient temperature. An aqueous solution of tartaric acid (2 mL), an aqueous solution of ammonium chloride (2 mL) and ether (10 mL) were added, the organic layer was separated and the aqueous phase was extracted with ether (3×15 mL). Combined organic layers were dried with anhydrous magnesium sulfate and solvents were evaporated in vacuo, yielding sufficiently pure crude title acid.

Yield: 120 mg (50%).

$R_F$ (SiO$_2$, dichloromethane/methanol 80:20) 0.80.

$^1$H NMR spectrum (200 MHz, CD$_3$COOD, $\delta_H$): 8.00 (d, J=3.2 Hz, 2H); 7.64 (bs, 1H); 7.61 (d, J=3.2 Hz, 2H); 7.44 (m, 1H); 7.41 (s, 1H); 6.92 (d, J=9.2 Hz, 1H); 4.84 (s, 2H); 2.35 (s, 3H).

The above acid (120 mg, 0.26 mmol) was dissolved in tetrahydrofuran/methanol/water mixture (1:5:1, 2 mL) and powdered L-lysine (40 mg, 0.25 mmol) was added. The mixture was stirred for 3 h and subsequently an excess of absolute ether (20 mL) was added. The formed suspension was stirred for 1 h, the precipitate was allowed to settle down and the solvent was decanted. The precipitate was washed with ether (4×20 mL) in the same way. The obtained L-lysinate of the title acid was dried in vacuo.

Yield: 129 mg (82%).

M.p. 136-143° C. (amorphous).

$^1$H NMR spectrum (200 MHz, DMSO-d$_6$, $\delta_H$): 7.97 (s, 4H); 7.70 (s, 2H); 7.36 (s, 4H); 6.82 (m, 1H); 4.32 (s, 2H); 3.21 (m, 2H); 2.72 (m, 2H); 2.17 (s, 3H); 1.74-1.28 (m, $\delta_H$).

Example 5

[4-[3,5-Bis-(3,4-dimethoxyphenylethynyl)phenylsulfanyl]-2-methylphenoxy]acetic acid

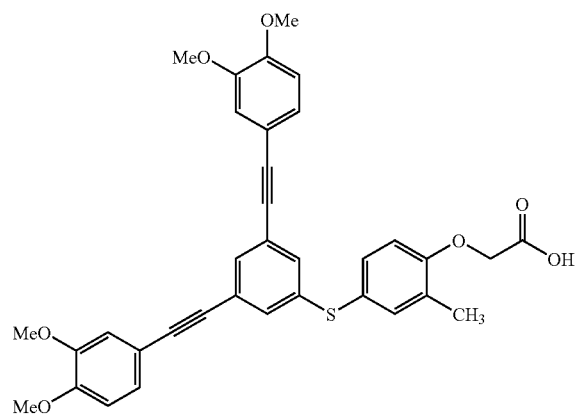

General Procedure (A)
Step B:

A solution of ethyl [4-(3,5-dibromophenylsulfanyl)-2-methylphenoxy]acetate (0.50 g, 1.10 mmol; prepared as described in example 1) and 1,2-dimethoxy-4-ethynylbenzene (360 mg, 2.20 mmol) in dry tetrahydrofuran (10 mL) was degassed and 0.15 M solution of tri-t-butylphospine in cyclohexane (0.730 mL, 0.11 mmol), copper(I)iodide (8 mg, 0.044 mmol), tris(dibenzylideneacetone)dipalladium chloroform complex (57 mg, 0.055 mmol) and N,N-diisopropylamine (0.25 mL, 2.20 mmol) were. The reaction flask was flushed with nitrogen again and the reaction mixture was stirred at 50° C. over night and for further 6 h at ambient temperature. The reaction solution was filtered through a short path of silica gel, silica gel was washed with ether (100 mL) and the combined filtrates were evaporated in vacuo. The residue was purified by column chromatography (silica gel Fluka 60: hexane/ethyl acetate 98:2-40:60) yielding ethyl [4-[3,5-bis-(3,4-dimethoxyphenylethynyl)phenylsulfanyl]-2-methylphenoxy]acetate.

Yield: 190 mg (28%).

$R_F$ (SiO$_2$, hexane/ethyl acetate 80:20) 0.15.

$^1$H NMR spectrum (200 MHz, CDCl$_3$, $\delta_H$): 7.36 (m, 1H); 7.33 (s, 1H); 7.25 (m, 1H); 7.13 (dd, J=8.3 and 1.8 Hz, 2H); 7.02 (d, J=1.8 Hz, 2H); 7.00-6.86 (m, 2H); 6.84 (d, J=8.4 Hz, 2 Hz); 6.72 (d, J=8.2 Hz, 1H); 4.67 (s, 2H); 4.28 (q, J=7.1 Hz, 2H); 3.19 (bs, 12H); 2.31 (s, 3H); 1.30 (t, J=7.3 Hz, 3H).

General Procedure (C)
Step A:

The above ester (190 mg, 0.305 mmol) was dissolved in tetrahydrofuran/methanol/water mixture (2:1:1, 5 mL), saturated solution of lithium hydroxide in water (0.5 mL) was added and the reaction mixture was stirred for 2 h at ambient temperature. A diluted solution of tartaric acid (2 mL) and ether (10 mL) were added, the organic layer was separated and the aqueous phase was extracted with ether (3×15 mL). Combined organic layers were dried with anhydrous magnesium sulfate and solvents were evaporated in vacuo yielding sufficiently pure crude title acid.

Yield: 80 mg (50%).

$R_F$ (SiO$_2$, dichloromethane/methanol 80:20) 0.75.

$^1$H NMR spectrum (200 MHz, CDCl$_3$, $\delta_H$): 7.50-6.56 (m, 14H); 4.82 (bs, 2H); 3.78 (bs, 12H); 2.01 (s, 3H).

The above acid (80 mg, 0.140 mmol) was dissolved in tetrahydrofuran/methanol/water mixture (1:5:1, 2 mL) and powdered L-lysine was added (21 mg, 0.150 mmol). The mixture was stirred for 3 h, absolute ether (20 ml) was added, the formed precipitate was allowed to settle down and solvents were decanted. The precipitate was washed with ether (4×20 mL) in the same way. The obtained L-lysinate of the title acid was dried in vacuo.

Yield: 58 mg (58%).

M.p. 148-151° C. (amorphous).

$^1$H NMR spectrum (200 MHz, DMSO-d$_6$, $\delta_H$): 8.32 (s, 1H); 7.65-6.89 (m, 11H); 6.82 (bd, J=8.8 Hz, 2 Hz); 4.33 (bs, 2H); 3.77 (bs, 12H); 3.23 (m, 1H); 2.71 (m, 2H); 2.17 (s, 3H); 1.78-1.22 (m, 7H).

Example 6

[4-[2,6-Bis-[(4-chlorophenyl)ethynyl]pyridine-4-ylsulfanyl]-2-methylphenoxy]acetic acid

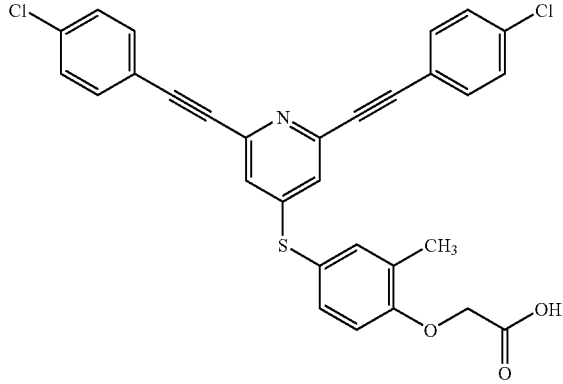

General Procedure (A)
Step A:

A mixture of ethyl (4-mercapto-2-methylphenoxy)acetate (1.0 g, 4.4 mmol), 2,4,6-tribromopyridine (1.26 g, 4 mmol; prepared as described in Chem. Ber. 1989, 122, 489), [1,1'-bis(diphenylphosphino)ferrocene]dichloropalladium complex with dichloromethane (0.163 g, 0.20 mmol), triethylamine (1.23 mL, 8.8 mmol) and N-methylpyrrolidinone (12 mL) was heated under nitrogen at 80° C. for 3 h. The reaction mixture was then poured into water (60 mL) and extracted with ethyl acetate (3×70 mL). The combined organic layers were dried with anhydrous magnesium sulfate and evaporated in vacuo. Column chromatography of the crude product (silica gel Fluka 60, hexanes/ethyl acetate 98:2-80:20) afforded ethyl [4-(2,6-dibromopyridine-4-ylsulfanyl)-2-methylphenoxy]acetate.

Yield: 1.33 g (72%).

$R_F$ (SiO$_2$, hexanes/ethyl acetate 90:10) 0.30.

$^1$H NMR spectrum (200 MHz, CDCl$_3$, $\delta_H$): 7.34-7.31 (m, 2H); 6.97 (s, 2H); 6.78 (d, J=9.1 Hz, 1H); 4.72 (s, 2H); 4.29 (q, J=7.1 Hz, 2H); 2.33 (s, 3H); 1.32 (t, J=7.1 Hz, 3H).

Step B:

In nitrogen atmosphere, the above ester (190 mg, 0.412 mmol) and 4-chloro-1-ethynylbenzene (169 mg, 1.24 mmol) were dissolved in anhydrous and degassed tetrahydrofuran (5 mL). A 0.15 M solution of tri-tert-butylphosphine in cyclohexane (0.327 mL, 0.049 mmol) was added via syringe. Copper(I) iodide (3.0 mg, 0.016 mmol), dichloro(bisbenzonitrile) palladium (9.6 mg, 0.025 mmol) and diisopropylamine (138 µL, 0.99 mmol) were added. The traces of the air were removed and the mixture was stirred under nitrogen at ambient temperature overnight. The mixture was diluted with ethyl acetate (20 mL) and filtered through a short path of silica gel. The filtrate was concentrated and purified by column chromatography (silica gel Fluka 60, hexanes/ethyl acetate 95:5-90:10) yielding ethyl [4-[2,6-bis[(4-chlorophenyl)ethynyl]pyridine-4-ylsulfanyl]-2-methylphenoxy]acetate.

Yield: 235 mg (99%).

$R_F$ (SiO$_2$, hexanes/ethyl acetate 75:25) 0.65.

$^1$H NMR spectrum (200 MHz, CDCl$_3$, $\delta_H$): 7.50 (d, J=8.6 Hz, 4H); 7.39-7.30 (m, $\delta_H$); 7.05 (s, 2H); 6.79 (d, J=9.1 Hz, 1H); 4.72 (s, 2H); 4.29 (q, J=7.1 Hz, 2H); 2.34 (s, 3H); 1.31 (t, J=7.1 Hz, 3H).

General Procedure (C)
Step A:

The above ester (228 mg, 0.398 mmol) was dissolved in tetrahydrofuran/methanol mixture (5:1, 9 mL), a solution of lithium hydroxide (25 mg, 0.597 mmol) in water (1 mL) was added under cooling (0° C.) and the reaction mixture was stirred for 2 h at ambient temperature. A solution of tartaric acid (89 mg, 0.597 mmol) in water (2 mL), saturated solution of ammonium chloride (2 mL), water (4 mL) and ether (10 mL) were added, the organic layer was separated and the aqueous phase was extracted with ether (3×10 mL). The combined organic layers were dried with anhydrous magnesium sulfate and solvents were evaporated in vacuo. The column chromatography (silica gel Fluka 60, dichloromethane/methanol 98:2-80:20) of the crude product afforded the title acid as white crystals.

Yield: 125 mg (58%).

M.p. 180-202° C. (amorphous).

$R_F$ (SiO$_2$, dichloromethane/methanol 90:10) 0.50.

$^1$H NMR spectrum (200 MHz, DMSO-d$_6$, $\delta_H$): 7.62 (d, J=8.5 Hz, 4H); 7.51 (d, J=8.5 Hz, 4H); 7.42 (d+s, J=7.6 Hz, 2H); 7.18 (s, 2H); 6.98 (d, J=8.4 Hz, 1H); 4.67 (s, 2H); 2.23 (s, 3H).

Example 7

[4-[2,6-Bis[(2-pyridyl)ethynyl]pyridine-4-ylsulfanyl]-2-methylphenoxy]acetic acid

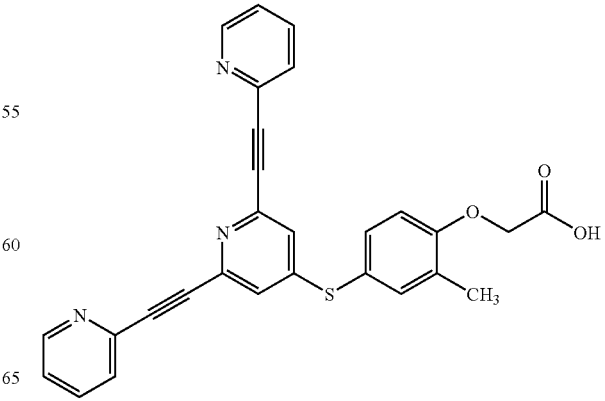

General Procedure (C)
Step B:

In nitrogen atmosphere, ethyl [4-(2,6-dibromopyridine-4-ylsulfanyl)-2-methylphenoxy]acetate (110 mg, 0.239 mmol; prepared as described in example 6) and 2-ethynylpyridine (74 mg, 0.717 mmol) were dissolved in degassed anhydrous tetrahydrofuran (2 mL). A 0.15 M Solution of tri-tert-butylphosphine in cyclohexane (0.191 mL, 0.029 mmol) was added via syringe. Copper(I) iodide (1.9 mg, 0.010 mmol), dichloro(bisbenzonitrile)palladium (5.5 mg, 0.014 mmol) and diisopropylamine (80 µL, 0.574 mmol) were subsequently added. The traces of air were removed and the mixture was stirred under nitrogen at ambient temperature overnight. The mixture was diluted with ethyl acetate (10 mL) and filtered through a short path of silica gel. The filtrate was concentrated and purified by column chromatography (silica gel Fluka 60, hexanes/ethyl acetate 9:1-1:9) yielding ethyl [4-[2,6-bis[(2-pyridyl)ethynyl]pyridine-4-ylsulfanyl]-2-methylphenoxy]acetate as a brown oil beside of a by-product-mono substituted derivative, ethyl [4-[6-bromo-2-[(2-pyridyl)ethynyl]pyridine-4-ylsulfanyl]-2-methylphenoxy]acetate (50 mg, 22% yield).

Yield: 105 mg (43%).

$R_F$ (SiO$_2$, dichloromethane/methanol 90:10) 0.70.

$^1$H NMR spectrum (300 MHz, CDCl$_3$, $\delta_H$): 8.61 (d, J=4.6 Hz, 2H); 7.68-7.59 (m, 4H); 7.36-7.25 (m, 4H); 7.17 (s, 2H); 6.78 (d, J=9.0 Hz, 1H); 4.72 (s, 2H); 4.28 (q, J=7.1 Hz, 2H); 2.33 (s, 3H); 1.30 (t, J=7.1 Hz, 3H).

General Procedure (C)
Step A:

The above ester (210 mg, 0.415 mmol) was dissolved in tetrahydrofuran/methanol mixture (5:1, 9 mL), a solution of lithium hydroxide monohydrate (26 mg, 0.623 mmol) in water (1 mL) was added under cooling (0° C.) and the reaction mixture was stirred for 2 h at ambient temperature. A solution of tartaric acid (100 mg, 0.664 mmol) in water (2 mL), saturated solution of ammonium chloride (4 mL), water (2 mL) and ether (10 mL) were added, the organic layer was separated and the aqueous phase was extracted with ether (3×10 mL). The combined organic layers were dried with anhydrous sodium sulfate and solvents were evaporated in vacuo. The crystallization of crude product from a mixture of acetonitrile and water afforded title acid as lightly brown crystals.

Yield: 142 mg (72%).

M.p. 190-193° C. (acetonitrile/water).

$R_F$ (SiO$_2$, dichloromethane/methanol 90:10) 0.25.

$^1$H NMR spectrum (300 MHz, DMSO-d$_6$, $\delta$): 8.64 (d, J=5.6 Hz, 2H); 7.92-7.86 (m, 2H); 7.72 (d, J=7.8 Hz, 2H); 7.50-7.46 (m, 4H); 7.26 (s, 2H); 7.04 (d, J=8.1 Hz, 1H); 4.83 (s, 2H); 2.25 (s, 3H).

Example 8

[2-Methyl-4-[2-(2-pyridylethynyl)-6-[(4-trifluoromethylphenyl)ethynyl]pyridine-4-ylsulfanyl]phenoxy] acetic acid

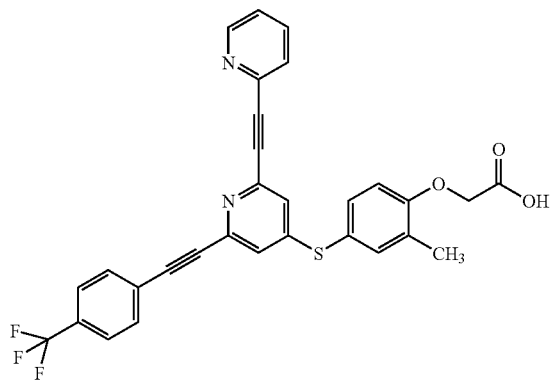

General Procedure (A)
Step B:

In nitrogen atmosphere, ethyl [4-(2,6-dibromopyridine-4-ylsulfanyl)-2-methyl-phenoxy]acetate (369 mg, 0.80 mmol, prepared as described in example 6) and 2-ethynylpyridine (91 mg, 0.88 mmol) were dissolved in degassed anhydrous tetrahydrofuran (7 mL). A 0.15 M Solution of tri-tert-butylphosphine in cyclohexane (0.64 mL, 0.096 mmol) was added via syringe. Copper(I) iodide (6.1 mg, 0.032 mmol), dichloro(bisbenzonitrile)palladium (18.4 mg, 0.048 mmol) and diisopropylamine (269 µL, 1.92 mmol) were subsequently added. The traces of air were removed and the mixture was stirred under nitrogen at ambient temperature overnight. The mixture was diluted with ethyl acetate (20 mL) and filtered through a short path of silica gel. The filtrate was concentrated and purified by column chromatography (silica gel Fluka 60, hexanes/ethyl acetate 9:1 to 1:9) yielding ethyl [4-[6-bromo-2-(2-pyridylethynyl)pyridine-4-ylsulfanyl]-2-methylphenoxy]acetate. The recovered starting material (119 mg, 32% yield) was used in further reactions as well as the disubstituted product, ethyl [4-[2,6-bis[(2-pyridyl)ethynyl]pyridine-4-ylsulfanyl]-2-methylphenoxy]acetate (67 mg, 17% yield).

Yield: 185 mg (48%).

$R_F$ (SiO$_2$, hexanes/ethyl acetate 75:25) 0.15.

$^1$H NMR spectrum (200 MHz, CDCl$_3$, $\delta_H$): 8.61 (d, J=4.8 Hz, 1H); 7.75-7.57 (m, 2H); 7.36-7.26 (m, 3H); 7.08 (d, J=1.5 Hz, 1H); 7.06 (d, J=1.5 Hz, 1H); 6.78 (d, J=9.1 Hz, 1H); 4.72 (s, 2H); 4.29 (q, J=7.2 Hz, 2H); 2.33 (s, 3H); 1.32 (t, J=7.2 Hz, 3H).

In nitrogen atmosphere, the above product (182 mg, 0.377 mmol) and (4-trifluoromethylphenyl)acetylene (96 mg, 0.565 mmol) were dissolved in degassed anhydrous tetrahydrofuran (4 mL). A 0.15 M Solution of tri-tert-butylphosphine in cyclohexane (0.300 mL, 0.045 mmol) was added via syringe. Copper(I) iodide (2.9 mg, 0.015 mmol), dichloro(bisbenzonitrile)palladium (8.7 mg, 0.023 mmol) and diisopropylamine (127 µL, 0.903 mmol) were subsequently added. The traces of air were removed and the mixture was stirred under nitrogen at ambient temperature overnight. The mixture was diluted with ethyl acetate (15 mL) and filtered through a short path of silica gel. The filtrate was concentrated and purified by column chromatography (silica gel Fluka 60, hexanes/ethyl acetate 9:14:6) yielding ethyl [2-methyl-4-(2-(2-pyridylethynyl)-6-[(4-trifluoromethylphenyl)ethynylpyridine-4-ylsulfanyl]-phenoxy]acetate.

Yield: 185 mg (86%).

$R_F$ (SiO$_2$, hexanes/ethyl acetate 1:1) 0.70.

$^1$H NMR spectrum (300 MHz, CDCl$_3$, $\delta_H$): 8.61 (d, J=4.6 Hz, 1H); 7.69-7.59 (m, 5H); 7.37-7.26 (m, 3H); 7.17 (s, 1H); 7.10 (s, 1H); 6.79 (d, J=8.9 Hz, 1H); 4.72 (s, 2H); 4.29 (q, J=7.1 Hz, 2H); 2.34 (s, 3H); 1.31 (t, J=7.1 Hz, 3H).

General Procedure (C)
Step A:

The above ester (185 mg, 0.323 mmol) was dissolved in tetrahydrofuran/methanol mixture (5:1, 9 mL), a solution of lithium hydroxide monohydrate (20 mg, 0.485 mmol) in water (1 mL) was added under cooling (0° C.) and the reaction mixture was stirred for 2 h at ambient temperature. A solution of tartaric acid (78 mg, 0.517 mmol) in water (2 mL), saturated solution of ammonium chloride (2 mL), water (4 mL)

and ether (10 mL) were added, the organic layer was separated and the aqueous phase was extracted with ether (3×10 mL). The combined organic layers were dried with anhydrous sodium sulfate and solvents were evaporated in vacuo. Column chromatography (silica gel Fluka 60, dichloromethane/methanol 100:0-5:15) of the crude product and crystallization from a mixture of acetonitrile, water and tetrahydrofuran afforded title acid as off-white crystals.

Yield: 100 mg (57%).

M.p. 120-123° C. (acetonitrile/water/tetrahydrofuran).

$R_F$ (SiO$_2$, dichloromethane/methanol 90:10) 0.35.

$^1$H NMR spectrum (300 MHz, DMSO-d$_6$, $\delta_H$): 8.62 (bs, 1H); 7.90-7.81 (m, 5H); 7.70 (d, J=7.5 Hz, 1H); 7.48-7.38 (m, 3H); 7.29 (s, 1H); 7.19 (s, 1H); 4.52 (s, 2H); 2.21 (s, 3H).

Example 9

[4-[3,5-Bis-(1-methyl-1H-pyrrol-2-ylethynyl)phenylsulfanyl]-2-methylphenoxy]acetic acid

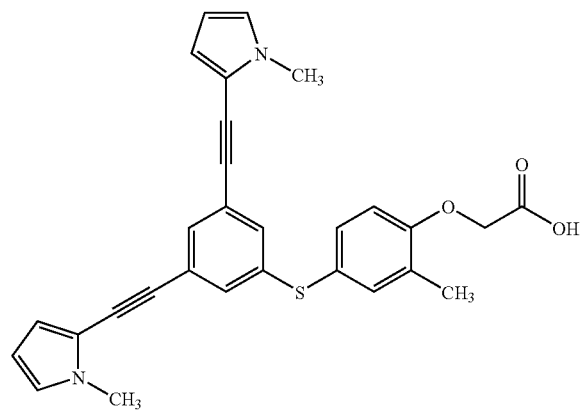

General Procedure (A)
Step B:

A solution of ethyl [4-[3,5-dibromophenylsulfanyl]-2-methylphenoxy]acetate (550 mg, 1.20 mmol; prepared as described in example 1) and 3-trimethylsilylethynyl-N-methylpyrrol (630 mg, 3.55 mmol) in tetrahydrofuran (5 mL) was degassed and than absolute ethanol (1 mL) and 1 M solution of tetrabutylammonium fluoride (3 mL, 3.00 mmol) were added. The mixture was stirred at ambient temperature for 1 h. A 0.15 M solution of tri-t-butyl-phosphine (0.8 mL, 0.12 mmol), copper(I)iodide (9 mg, 0.05 mmol), tris(dibenzylideneacetone) dipalladium chloroform complex (62 mg, 0.06 mmol) and N,N-diisopropylamine (0.50 mL, 4.80 mmol) were added. The reaction flask was flushed with nitrogen again and the reaction mixture was stirred at 60° C. for 5 h. After all the reaction solution was filtered through a short path of silica gel, silica gel was washed with ether (100 mL) and the combined filtrates were evaporated in vacuo. The residue was purified by column chromatography (silica gel Fluka 60: hexane/ethyl acetate/triethylamine 98:2:0.05-90:10:0.05) yielding [4-[3,5-bis-(1-methyl-1H-pyrrol-2-ylethynyl)phenylsulfanyl]-2-methylphenoxy]acetate.

Yield: 0.43 g (70%).

$R_F$ (SiO$_2$, hexane/ethyl acetate 80:20) 0.45.

$^1$H NMR spectrum (250 MHz, CDCl$_3$, $\delta_H$): 7.36 (bt, J=1.4 Hz, 1H); 7.32-7.26 (m, 2H); 7.19 (bd, J=1.5 Hz, 2H); 6.71 (d, J=8.2 Hz, 1H); 6.68 (dd, J=2.7, 1.7 Hz, 2H); 6.47 (dd, J=3.8, 1.7 Hz; 2H); 6.10 (dd, J=3.8, 2.7 Hz; 2H); 4.66 (s, 2H); 4.26 (q, J=7.2 Hz, 2H); 3.71 (s, 6 H); 2.29 (s, 3H); 1.29 (t, J=7.1 Hz, 3H).

General Procedure (C)
Step A:

A solution of lithium hydroxide monohydrate (0.05 g, 1.00 mmol) in distilled water (1 mL) was added to an ice-water cooled solution of the above ester (0.43 g, 0.85 mmol) in a mixture tetrahydrofuran/methanol (5:1; 6 mL) and the resulting solution was stirred for 45 min under cooling. The reaction mixture was neutralized with saturated solution of tartaric acid (5 mL) and saturated solution of ammonium chloride (5 mL) and water (10 mL) were added. The solution was extracted with chloroform (4×20 mL), combined organic layers were dried with anhydrous magnesium sulfate and evaporated in vacuo. This afforded [4-[3,5-bis-[3-(morpholine-4-yl)propynyl] phenylsulfanyl]-2-methylphenoxy]acetic acid sufficiently pure.

Yield: 400 mg (98%).

$R_F$ (SiO$_2$, dichloromethane/methanol 80:20) 0.55.

$^1$H NMR spectrum (250 MHz, CDCl$_3$, $\delta_H$): 7.37 (t, J=1.4 Hz, 1H); 7.30-7.26 (m, 2H); 7.20 (d, J=1.4 Hz, 2H); 6.73 (d, J=8.2 Hz, 1H); 6.67 (dd, J=2.6, 1.7 Hz; 2H); 6.47 (dd, J=3.8, 1.7 Hz; 2H); 6.10 (dd, J=3.8, 2.7 Hz; 2H); 4.70 (s, 2H); 3.70 (s, $\delta_H$); 2.28 (s, 3H).

A solution of L-lysine (120 mg, 0.83 mmol) in distilled water (0.8 mL) was added to a solution of the above acid (400 mg, 0.83 mmol) in tetrahydrofuran (8 mL) and methanol (4 mL) mixture. The resulting solution was stirred for 60 min and evaporated in vacuo. The residue was dissolved in a minimal amount of methanol and dry acetonitrile (50 mL) was added. After filtering off the precipitate was washed with anhydrous ether (50 mL) yielding L-lysinate of the title acid.

Yield: 150 mg (29%).

M.p. 128-135° C. (amorphous).

$^1$H NMR spectrum (250 MHz, DMSO-d$_6$, $\delta_H$): 7.42 (m, 1H); 7.33 (m, 2H); 7.13 (m, 2H); 6.94 (m, 2H); 6.83 (m, 1H); 6.46 (m, 2H); 6.05 (m, 2H); 4.33 (m, 2H); 3.68 (m, 2H); 3.50 (m, 1H); 2.77 (m, 2H); 2.19 (s, 3H); 1.84-1.22 (m, ~4).

Example 10

[2-Methyl-4-[2,6-bis[(4-trifluoromethylphenyl)ethynyl]pyridyl-4-sulfanyl]phenoxy]acetic acid

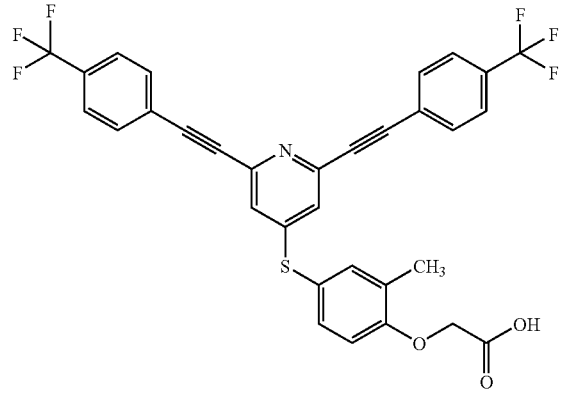

In nitrogen atmosphere, ethyl [4-(2,6-dibromopyridyl-4-sulfanyl)-2-methylphenoxy]-acetate (461 mg, 1.0 mmol; prepared as described in example 6) and 4-(trifluoromethyl) phenylacetylene (255 mg, 1.5 mmol) were dissolved in anhydrous and degassed tetrahydrofuran (8 mL). A 0.15 M solution of tri-tert-butylphosphine in cyclohexane (0.80 mL, 0.12 mmol) was added via syringe. Copper(I) iodide (7.6 mg, 0.04 mmol), dichloro(bisbenzonitrile)palladium (23 mg, 0.06 mmol) and diisopropylamine (336 μL, 2.4 mmol) were added, the traces of the air were removed and the mixture was stirred under nitrogen at ambient temperature overnight. The reaction mixture was diluted with ethyl acetate (20 mL) and filtered through a short path of silica gel. The filtrate was concentrated and purified by column chromatography (silica gel Fluka 60, hexanes/ethyl acetate from 99:1 to 90:10) yielding a mixture of the monosubstituted product ethyl [2-methyl-4-[6-bromo-2-[(4-trifluoromethylphenyl)ethynyl]pyridyl-4-sulfanyl]phenoxy]acetate and the disubstituted product ethyl [2-methyl-4-[2,6-bis[(4-trifluoromethylphenyl)ethynyl]pyridyl-4-sulfanyl]-phenoxy]acetate (overall yield: 450 mg). The whole mixture was further treated in subsequent Sonogashira reaction with N-propargylmorpholine to finally isolate the disubstituted product.

Yield: 210 mg (33%; disubstituted product).

$R_F$ (SiO$_2$, hexanes/ethyl acetate 90:10) 0.30.

$^1$H NMR spectrum (300 MHz, CDCl$_3$, $\delta_H$): 7.67 (d, J=8.4 Hz, 4H); 7.61 (d, J=8.4 Hz, 4H); 7.39-7.36 (m, 2H); 7.10 (s, 2H); 6.80 (d, J=8.9 Hz, 1H); 4.72 (s, 2H); 4.29 (q, J=7.1 Hz, 2H); 2.34 (s, 3H); 1.31 (t, J=7.1 Hz, 3H).

General Procedure (C)
Step A:

The above ester (210 mg, 0.328 mmol) was dissolved in tetrahydrofuran/methanol mixture (5:1, 9 mL), a solution of lithium hydroxide (21 mg, 0.492 mmol) in water (1 mL) was added under cooling (0° C.) and the reaction mixture was stirred for 2 h at ambient temperature. A solution of tartaric acid (79 mg, 0.525 mmol) in water (2 mL), saturated solution of ammonium chloride (4 mL), water (2 mL) and ether (10 mL) were added, the organic layer was separated and the aqueous phase was extracted with ether (3×10 mL). The combined organic layers were dried with anhydrous sodium sulfate and solvents were evaporated in vacuo. The crystallization of the crude product from a mixture of acetonitrile and water afforded the title acid as white crystals.

Yield: 105 mg (53%).

M.p. 198-206° C. (amorphous).

$R_F$ (SiO$_2$, dichloromethane/methanol/triethylamine 90:10: 0.5) 0.50.

$^1$H NMR spectrum (300 MHz, DMSO-d$_6$, $\delta_H$): 13.13 (bs, 1H); 7.83 (s, 8H); 7.49-7.46 (m, 2H); 7.28 (s, 2H); 7.03 (d, J=8.3 Hz, 1H); 4.81 (s, 2H); 2.25 (s, 3H).

Example 11

{7-[2,6-Bis-(4-chloro-phenylethynyl)-pyridin-4-ylsulfanyl]-indan-4-yloxy}-acetic acid

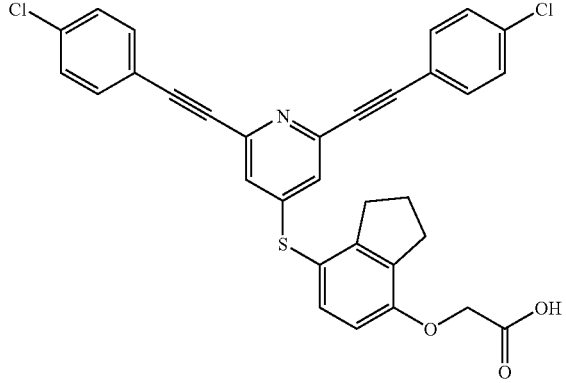

General Procedure (A)
Step A:

1,3,5-Tribromopyridine (3.3 g, 10.5 mmol), 1,1'-bis(diphenylphosphino)ferrocene (0.35 g, 0.63 mmol) and tris(dibenzylideneacetone)dipalladium (0) (0.28 g, 0.31 mmol were added to a dried reaction flask under an atmosphere of nitrogen. Dry NMP (80 ml) was added followed by TEA (3.7 ml) and (7-mercapto-indan-4-yloxy)-acetic acid methyl ester (2.5 g, 10.5 mmol) pre-dissolved in dry NMP (20 ml). The reaction mixture was heated to 60° C. for 2½ h and cooled to room temperature. Saturated sodium chloride (200 ml), water (200 ml), 5% aqueous citric acid (30 ml) and ethyl acetate (about 300 ml) was added and to the reaction mixture. The organic phase was separated form the aqueous phase and the aqueous phase was extracted with ethyl acetate (200 ml). The pooled organic phase was washed with a mixture of saturated sodium chloride (30 ml) and water (30 ml) and the organic phase dried and evaporated to dryness. The crude product was purified by flash chromatography (ethyl acetate:heptane; 1:20→1:10) to give 7-(2,6-dibromo-pyridin-4-ylsulfanyl)-indan-4-yloxy]-acetic acid methyl ester as a white solid. Yield: (2.0 g; 40%).

LC-MS (system 1): Rt: 2.60 min; Mw: 474.2

Step B:

7-(2,6-Dibromo-pyridin-4-ylsulfanyl)-indan-4-yloxy]-acetic acid methyl ester (0.2 g; 0.42 mmol), cupper iodide (3.2 mg; 0.017 mmol), 4-chlorphenylacetylene (86.6 mg; 0.63 mmol) and bis(triphenylphosphine) palladium (II) chloride (12 mg; 0.017 mmol) were added to a dry reaction flask under an atmosphere of nitrogen. Bis-(tri-t-butylphosphine)palladium (0) (13 mg; 0.025 mmol), diisopropylamine (0.10 ml; 0.72 mmol) and dioxane (10 ml) was added and the reaction mixture was stirred at 40° C. for 18 h. The reaction mixture was evaporated and purified by flash chromatography (ethyl acetate) and preparative HPLC (method B) to give [7-[2,6-bis-(4-chloro-phenylethynyl)-pyridine-4-ylsulfanyl]-indan-4-yloxy]-acetic acid methyl ester. Yield: 100 mg; 45%.

LC-MS (system 1): Rt: 3.19 min.; Mw: 584.1.

General Procedure (C)
Step A:

{7-[2,6-Bis-(4-chloro-phenylethynyl)-pyridine-4-ylsulfanyl]-indan-4-yloxy}-acetic acid methyl ester (100 mg; 0.17 mmol) was dissolved in a mixture of THF and ethanol (1:2) (30 ml) and 1N sodium hydroxide (1.5 ml) was added. The reaction mixture was stirred for about 1 h and 1N aqueous hydrogen chloride (3 ml), water (10 ml) and ethyl acetate (20 ml) was added. The organic phase was separated from the aqueous phase and the aqueous phase was extracted with ethyl acetate (10 ml). The pooled organic phases were washed with water (10 ml), dried and evaporated to dryness to give {7-[2,6-bis-(4-chloro-phenylethynyl)-pyridin-4-ylsulanyl]-indan-4-yloxy}-acetic acid. Yield: 80 mg.

LC-MS (system 1): Rt: 3.07 min.; Mw: 570.4.

Example 12

{7-[2,6-Bis-(4-hydroxymethyl-phenylethynyl)-pyridin-4-ylsulfanyl]-indan-4-yloxy}-acetic acid

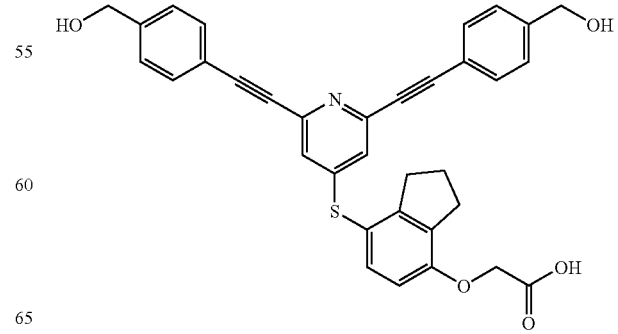

General Procedure (A)
Step B:

7-(2,6-Dibromo-pyridin-4-ylsulfanyl)-indan-4-yloxy]-acetic acid methyl ester (0.1 g; 0.21 mmol, prepared as described in example 11), cupper iodide (1.2 mg; 0.006 mmol), 4-ethynylbenzyl alcohol (83.8 mg; 0.63 mmol) and bis(triphenylphosphine) palladium (II) chloride (5.9 mg; 0.008 mmol) were added to a dry reaction flask under an atmosphere of nitrogen. Triethylamine (4 ml) was added and the reaction mixture was stirred at 40° C. for 2 days. The reaction mixture was evaporated and purified by preparative HPLC (method A) to give {7-[2,6-bis-(4-hydroxymethyl-phenylethynyl)-pyridine-4-ylsulfanyl]-indan-4-yloxy}-acetic acid methyl ester. Yield: 25 mg.

LC-MS (system 1): Rt: 2.09 min.; Mw: 562.5

General Procedure (C)
Step A:

{7-[2,6-Bis-(4-hydroxymethyl-phenylethynyl)-pyridine-4-ylsulfanyl]-indan-4-yloxy}-acetic acid methyl ester (70 mg; 0.12 mmol) was dissolved in a mixture of THF and ethanol (1:2) (30 ml) and 1N sodium hydroxide (1 ml) was added. The reaction mixture was stirred for about 16 h and 1N aqueous hydrogen chloride (2 ml), water (10 ml) and ethyl acetate (20 ml) were added. The organic phase was separated from the aqueous phase and the aqueous phase was extracted with ethyl acetate (10 ml). The pooled organic phases were washed with water (10 ml), dried and evaporated to dryness to give {7-[2,6-bis-(4-hydroxymethyl-phenylethynyl)-pyridin-4-ylsulfanyl]-indan-4-yloxy}-acetic acid. Yield: 64 mg LC-MS (system 1): Rt: 2.09; Mw: 562.5.

Example 13

{4-[2,6-bis-(4-hydroxymethyl-phenylethynyl)-pyridin-4-ylsulfanyl]-2-methyl-phenoxy}-acetic acid

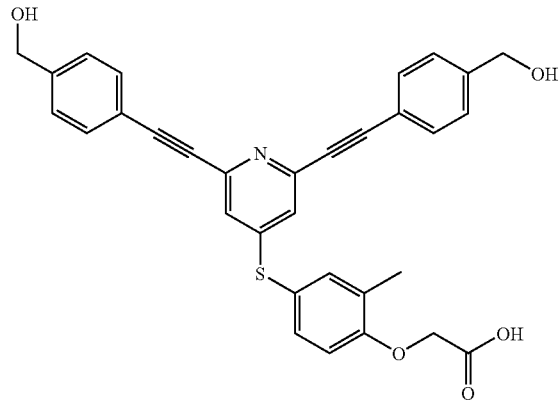

General Procedure (A)
Step B:

7-(2,6-Dibromo-pyridin-4-ylsulfanyl)-2-methyl-phenoxy}-acetic acid methyl ester (0.3 g; 0.67 mmol, prepared as described in example 6), cupper iodide (3.8 mg; 0.02 mmol), 4-ethynylbenzylalcohol (266 mg; 2.01 mmol) and bis(triphenylphosphine) palladium (II) chloride (18.8 mg; 0.027 mmol) were added to a dry reaction flask under an atmosphere of nitrogen. Triethylamine (2 ml) and DMF (2 ml) was added and the reaction mixture was reacted at 70° C. for 10 min in a microwave oven. The reaction mixture was purified by preparative HPLC (method B) to give {4-[2,6-bis-(4-hydroxym-ethyl-phenylethynyl)-pyridin-4-ylsulfanyl]-2-methyl-phenoxy}-acetic acid methyl ester. Yield: 260 mg; 70%.

LC-MS (system 1): Rt: 3.02 min.; Mw: 576.4.

General Procedure (C)
Step A:

{4-[2,6-Bis-(4-hydroxymethyl-phenylethynyl)-pyridin-4-ylsulfanyl]-2-methyl-phenoxy}-acetic acid methyl ester (150 mg; 0.27 mmol) was dissolved in a mixture of THF and ethanol (1:1) (10 ml) and 1N sodium hydroxide (1.5 ml) was added. The reaction mixture was stirred for about 1 h and 1N aqueous hydrogen chloride (3 ml), water (10 ml) and ethyl acetate (20 ml) was added. The organic phase was separated from the aqueous phase and the aqueous phase was extracted with ethyl acetate (10 ml). The pooled organic phases were washed with water (10 ml), dried and evaporated. During the evaporation a solid was formed which was filtered off and dried to give {4-[2,6-bis-(4-hydroxymethyl-phenylethynyl)-pyridin-4-ylsulfanyl]-2-methyl-phenoxy}-acetic acid. Yield: 51 mg.

LC-MS (system 1): Rt: 1.2 min.; Mw: 536.1.

Example 14

{4-[2,6-bis-(2-hydroxymethyl-phenylethynyl)-pyridin-4-ylsulfanyl]-2-methyl-phenoxy}-acetic acid

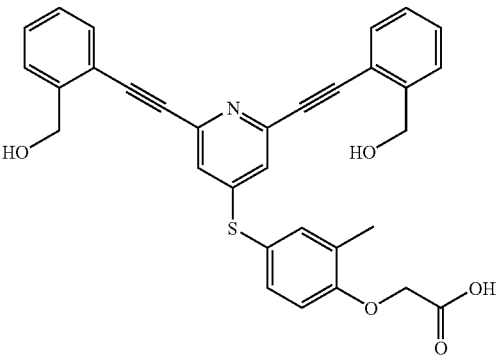

General Procedure (A)
Step B:

7-(2,6-Dibromo-pyridin-4-ylsulfanyl)-2-methyl-phenoxy}-acetic acid methyl ester (0.15 g; 0.33 mmol), cupper iodide (1.8 mg; 0.01 mmol), 2-ethynylbenzylalcohol (128 mg; 0.98 mmol) and bis(triphenylphosphine) palladium (II) chloride (9.1 mg; 0.013 mmol) were added to a dry reaction flask under an atmosphere of nitrogen. Triethylamine (1 ml) and DMF (1 ml) was added and the reaction mixture was reacted at 70° C. for 10 min in a microwave oven. The reaction mixture was purified by preparative HPLC (method B) to give {4-[2,6-bis(3-hydroxymethyl-phenylethynyl)-pyridin-4-yl-sulfanyl]-2-methyl-phenoxy}-acetic acid methyl ester. Yield: 51 mg.

LC-MS (system 1): Rt: 2.3 min.; Mw: 624.6.

General Procedure (C)
Step A:

{4-[2,6-Bis-(2-hydroxymethyl-phenylethynyl)-pyridin-4-ylsulfanyl]-2-methyl-phenoxy}-acetic acid methyl ester (51 mg; 0.090 mmol) was dissolved in a mixture of THF and ethanol (2:1) (10 ml) and 1N sodium hydroxide (0.5 ml) was added. The reaction mixture was stirred for about 1 h and 1N aqueous hydrogen chloride (3 ml), water (10 ml) and ethyl acetate (20 ml) was added. The organic phase was separated from the aqueous phase and the aqueous phase was extracted with ethyl acetate (10 ml). The pooled organic phases were washed with water (10 ml), dried and evaporated to dryness. The crude product was purified by prep. HPLC to give {4-[2,6-bis-(2-hydroxymethyl-phenylethynyl)-pyridin-4-ylsulfanyl]-2-methyl-phenoxy}-acetic acid. Yield: 23 mg.

LC-MS (system 1): Rt: 2.04 Mw: 536.1.

Example 15

[4-[3,5-Bis-[(4-trifluoromethylphenyl)ethynyl]benzyloxy]-2-methylphenoxy]acetic acid

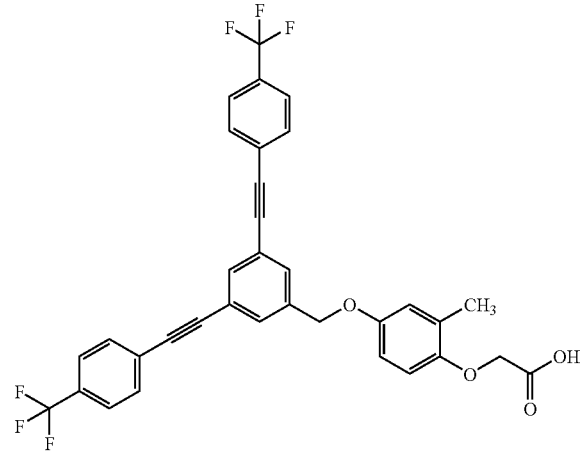

3,5-Dibromobenzaldehyde (1.7 g, 6.3 mmol) was dissolved in methanol (100 mL) and sodium borohydride (0.250 g, 6.3 mmol) was added at 0° C. The reaction mixture was stirred for 0.5 h at 0° C. and then at 20° C. for another 0.5 h. The reaction mixture was concentrated in vacuo, diluted with brine (250 mL), acidified with hydrochloric acid and extracted with dichloromethane (3×50 mL). Evaporation of the organic solution gave 3,5-dibromo-benzyl alcohol as a white crystalline compound.

Yield: 1.4 g (84%).

$R_F$ (SiO$_2$, hexanes/ethyl acetate 9:1) 0.25.

$^1$H NMR spectrum (300 MHz, CDCl$_3$, A) 7.59 (d, J=1.5 Hz, 1H); 7.47 (d, J=1.5 Hz, 2H); 4.36 (s, 2H); 1.55 (s, 1H).

The above benzyl alcohol (0.26 g, 1.0 mmol) and methyl (4-hydroxy-2-methylphenoxy)acetate (0.30 g, 1.5 mmol) and triphenylphosphine (0.50 g, 1.85 mmol) were dissolved in a mixture of anhydrous toluene (3-mL) and tetrahydrofuran (1 mL) and the mixture was cooled to 0° C. Diisopropyl azodicarboxylate (0.22 g, 1.2 mmol) was added dropwise under nitrogen. The reaction mixture was stirred for 12 h at ambient temperature and the solvents were evaporated in vacuo. Column chromatography (silica gel Fluka 60, hexanes/ethyl acetate 98:2-90:10) gave methyl [4-(3,5-dibromo)benzyloxy]-2-methylphenoxy]acetate.

Yield: 0.25 g (56%).

$R_F$ (SiO$_2$, hexanes/ethyl acetate 8:2) 0.45.

$^1$H NMR spectrum (300 MHz, CDCl$_3$, $\delta_H$): 7.61 (s, 1H); 7.48 (s, 2H); 6.80 (s, 2H); 6.67 (s, 2H); 4.92 (s, 2H); 4.60 (s, 2H); 3.80 (s, 3H); 2.28 (s, 3H).

Copper(I) iodide (4 mg, 0.02 mmol), tris(dibenzylideneacetone)dipalladium chloroform complex (26 mg, 0.025 mmol), 0.15 M solution of tri-t-butylphosphine (0.33 mL, 0.05 mmol) and N,N-diisopropylamine (0.1 mL, 1.00 mmol) were added to a degassed mmol) and N,N-diisopropylamine (0.1 mL, 1.00 mmol) were added to a degassed solution of the above ester (0.25 g, 0.5 mmol) and 1-ethynyl-4-(trifluoromethyl)benzene (0.17 g, 1.00 mmol) in dry tetrahydrofuran (10 mL). In atmosphere of nitrogen, the resulting mixture was stirred at 60° C. overnight. The reaction mixture was filtered through a short path of silica gel, silica gel was washed with ether (100 mL) and the combined filtrates were evaporated in vacuo. The residue was purified by column chromatography (silica gel Fluka 60, hexanes/ethyl acetate 98:2-90:10) yielding methyl [4-[3,5-bis-[(4-trifluoromethylphenyl)ethynyl]benzyloxy]-2-methylphenoxy]acetate.

Yield: 0.25 g (90%).

$R_F$ (SiO$_2$, hexanes/ethyl acetate 8:2) 0.40.

The above compound (0.120 g, 0.19 mmol) was dissolved in tetrahydrofuran/methanol mixture (3:1; 4 mL) and aqueous solution of lithium hydroxide (0.013 g, 0.30 mmol in 1 mL water) was added. After 1 h at 20° C. the mixture was acidified with hydrochloric acid and extracted with dichloromethane (3×10 mL).

The obtained sufficiently pure acid (0.080 g, 0.13 mmol) was dissolved in methanol (2 mL) and aqueous solution of L-lysine (0.025 g, 0.18 mmol) in water (1 mL) was added. Precipitation with acetonitrile gave the L-lysinate of the title acid (acid:L-lysine ratio 1:1.2).

Yield: 0.030 g (31%).

$R_F$ (SiO$_2$, dichloromethane/methanol 90:10) 0.80.

$^1$H NMR spectrum (300 MHz, DMSO-d$_6$, $\delta_H$): 7.79 (s, 9H); 7.70 (s, 2H); 6.90-6.65 (m, 3H); 5.07 (s, 2H); 4.54 (bs, 2H); 2.15 (s, 3H); 1.60-1.00 (m, 7.2H).

Example 16

[4-[3,5-Bis[(2-thienyl)ethynyl]benzyloxy]-2-methylphenoxy]acetic acid

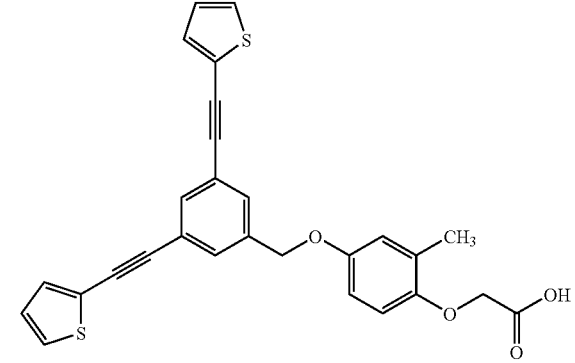

Trimethylsilylacetylene (420 μL, 3.0 mmol) was added to a mixture of methyl [4-(3,5-dibromobenzyloxy)-2-methylphenoxy]acetate (444 mg, 1.0 mmol; prepared as described in example 15), copper(I) iodide (13 mg, 0.07 mmol) and tetrakis(triphenylphosphine)palladium (35 mg, 0.03 mmol) in dry triethylamine (8 mL). The reaction mixture was stirred for 3 h at 70° C. and then at ambient temperature overnight. The resulting mixture was evaporated in vacuo, the residue was dissolved in ether/ethyl acetate mixture (1:1, 20 mL) and the formed precipitate was filtered off. The filtrate was evaporated in vacuo to yield red-brown oil. Potassium carbonate (23 mg, 0.17 mmol), dry methanol (2 mL) and dry dichloromethane (2 mL) were added to the oil under nitrogen and the resulting mixture was stirred for 3 h. Dichloromethane (15 mL) was added and the mixture was washed with brine (15 mL). The aqueous layer was extracted with dichloromethane (2×10 mL); the combined organic layers were dried with anhydrous sodium sulfate and evaporated in vacuo. The crude product was purified by column chromatography (silica gel Fluka 60, hexanes/ethyl acetate 90:10-80:20) yielding methyl [4-(3,5-diethynylbenzyloxy)-2-methylphenoxy]acetate.

Yield: 184 mg (55%).

M.p.: - - - (oil).

$R_F$ (SiO$_2$, hexanes/ethyl acetate 9:1) 0.20.

$^1$H NMR spectrum (300 MHz, CDCl$_3$, $\delta_H$): 7.55 (s, 1H); 7.52 (s, 2H); 6.80 (d, J=2.6 Hz, 1H); 6.69 (d, J=8.9 Hz, 1H); 6.65 (d, J=9.0 Hz, 1H); 4.94 (s, 2H); 4.60 (s, 2H); 3.39 (s, 3H); 3.09 (s, 2H); 2.28 (s, 3H).

In nitrogen atmosphere, the above ester (180 mg, 0.538 mmol) and 2-bromothiophene (202 mg, 1.238 mmol) were dissolved in anhydrous and degassed tetrahydrofuran (4 mL). A 0.15 M Solution of tri-tert-butylphosphine in cyclohexane (0.43 mL, 0.065 mmol) was added via syringe. Copper(I) iodide (4.1 mg, 0.022 mmol), tris(dibenzylideneacetone)dipalladium chloroform complex (16.5 mg, 0.032 mmol) and diisopropylamine (131 µL, 1.29 mmol) were added. The traces of the air were removed and the mixture was stirred under nitrogen at ambient temperature overnight. The mixture was diluted with ethyl acetate (10 mL) and washed with brine (2×10 mL). The organic layer was dried with anhydrous magnesium sulfate and evaporated in vacuo. The crude product was purified by column chromatography (silica gel Ruka 60, hexanes/ethyl acetate 98:2-90:10) yielding methyl [4-[3,5-bis[(2-thienyl)ethynyl]benzyloxy]-2-methylphenoxy]acetate as slightly orange solid mass.

Yield: 201 mg (75%).

$R_F$ (SiO$_2$, hexanes/ethyl acetate 80:20) 0.50.

$^1$H NMR spectrum (300 MHz, CDCl$_3$, $\delta_H$): 7.61 (s, 1H); 7.52 (s, 1H); 7.32-7.29 (m, 4H); 7.02 (dd, J=5.1 and 3.7 Hz, 2H); 6.83 (s, 1H); 6.70-6.64 (m, 2H); 4.98 (s, 2H), 4.60 (s, 2H); 3.80 (s, 3H); 2.29 (s, 3H).

The above ester (190 mg, 0.381 mmol) was dissolved in tetrahydrofuran/methanol mixture (5:1, 9 mL); a solution of lithium hydroxide monohydrate (24 mg, 0.571 mmol) in water (1 mL) was added under cooling (0° C.) and the reaction solution was subsequently stirred at ambient temperature overnight. The mixture was diluted with ether (10 mL) and washed with saturated aqueous solution of ammonium chloride (10 mL). The aqueous layer was extracted with ether (2×10 mL). The combined organic layers were dried with anhydrous sodium sulfate and evaporated in vacuo. The crude product was crystallized from hexanes/ethyl acetate mixture (1:1) yielding the title acid as white crystals.

Yield: 121 mg (65%).

M.p.: 127-129° C. (hexanes/ethyl acetate 1:1).

$R_F$ (SiO$_2$, dichloromethane/methanol 90:10) 0.40.

$^1$H NMR spectrum (300 MHz, CDCl$_3$, 6H): 7.62 (s, 1H); 7.52 (s, 2H); 7.32-7.28 (m, 4H); 7.02 (dd, J=5.1 and 3.7 Hz, 2H); 6.84 (s, 1H); 6.71 (m, 2H); 4.99 (s, 2H); 4.63 (d, 2H); 2.28 (s, 3H).

Example 17

[4-[4,6-Bis[(4-trifluoromethylphenyl)ethynyl]pyridin-2-ylsulfanyl]-2-methylphenoxy]acetic acid

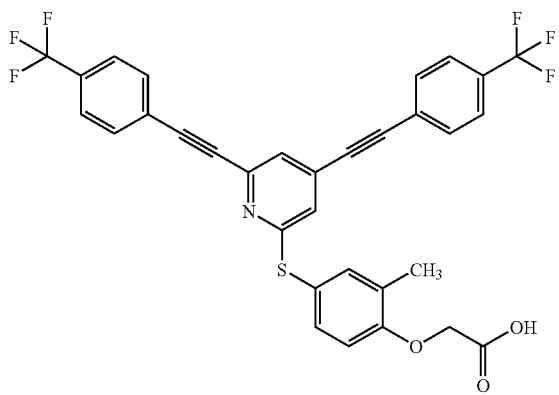

A mixture of ethyl (4-mercapto-2-methylphenoxy)acetate (1.0 g, 4.4 mmol), 2,4,6-tribromopyridine (1.26 g, 4.0 mmol; prepared as described in Chem. Ber. 1989, 122, 489), [1,1'-bis(diphenylphosphino)ferrocene]dichloropalladium dichloromethane complex (0.163 g, 0.20 mmol), triethylamine (1.23 mL, 8.8 mmol) and N-methylpyrrolidinone (12 mL) was heated under nitrogen at 80° C. for 3 h. The reaction mixture was then poured into water (60 mL) and extracted with ethyl acetate (3×70 mL). The combined organic layers were dried with anhydrous magnesium sulfate and evaporated in vacuo. Column chromatography of the crude product (silica gel Fluka 60, hexanes/ethyl acetate 98:2-80:20) afforded ethyl [4-(4,6-dibromopyridin-2-ylsulfanyl)-2-methylphenoxy]acetate as the minor product and ethyl [4-(2,6-dibromopyridin-4-ylsulfanyl)-2-methylphenoxy]acetate as the major product.

Yield of the major product: 1.33 g (72%).

Yield of the minor product: 0.076 g (4%).

$R_F$ (SiO$_2$, hexanes/ethyl acetate 90:10) 0.30 (the minor product).

In nitrogen atmosphere, the above minor ester (76 mg, 0.165 mmol) and 4-(trifluoromethyl)phenylacetylene (84 mg, 0.495 mmol) were dissolved in anhydrous and degassed tetrahydrofuran (2 mL). A 0.15 M solution of tri-tert-butylphosphine in cyclohexane (0.132 mL, 0.02 mmol) was added via syringe. Copper(I) iodide (2.0 mg, 0.01 mmol), dichloro(bis-benzonitrile)palladium (3.8 mg, 0.01 mmol) and diisopropylamine (336 µL, 0.33 mmol) were added. The traces of the air were removed and the mixture was stirred under nitrogen at ambient temperature overnight. The mixture was diluted with ethyl acetate (10 mL) and filtered through a short path of silica gel. The filtrate was concentrated and purified by column chromatography (silica gel Fluka 60, hexanes/ethyl acetate 99:1-90:10) yielding ethyl [4-[4,6-bis[(4-trifluoromethylphenyl)ethynyl]pyridin-2-ylsulfanyl]-2-methylphenoxy]acetate as brown oil.

Yield: 70 mg (66%).

$R_F$ (SiO$_2$, hexanes/ethyl acetate 90:10) 0.30.

$^1$H NMR spectrum (300 MHz, CDCl$_3$, $\delta_H$): 7.69 (d, J=8.3 Hz, 2H); 7.62 (d, J=8.3 Hz, 2H); 7.61 (s, 4H); 7.45-7.42 (m, 2H); 7.34 (s, 1H); 6.79 (d, J=8.1 Hz, 1H); 6.75 (s, 1H); 4.71 (s, 2H); 4.28 (q, J=7.1 Hz, 2H); 2.34 (s, 3H); 1.31 (t, J=7.1 Hz, 3H).

The above ester (60 mg, 0.094 mmol) was dissolved in tetrahydrofuran/methanol mixture (5:1, 1.8 mL), a solution of lithium hydroxide (5.9 mg, 0.141 mmol) in water (0.2 mL) was added under cooling (0° C.) and the reaction mixture was stirred for 2 h at ambient temperature. The mixture was diluted with ethyl acetate (10 mL) and washed with saturated aqueous solution of ammonium chloride (10 mL). The organic layer was separated and the aqueous phase was extracted with ethyl acetate (2×10 mL). The combined organic layers were dried with anhydrous sodium sulfate and the solvents were evaporated in vacuo yielding sufficiently pure title acid as brownish oil.

Yield: 57 mg (99%).

$R_F$ (SiO$_2$, dichloromethane/methanol 90:10) 0.40.

$^1$H NMR spectrum (300 MHz, DMSO-d$_6$, $\delta_H$): 7.87-7.80 (m, 8H); 7.66 (s, 1H); 7.47-7.44 (m, 2H); 6.99 (d, J=8.2 Hz, 1H); 6.85 (s, 1H); 4.76 (s, 2H); 2.24 (s, 3H).

Example 18

{4-[2,6-Bis-(4-trifluoromethyl-phenylethynyl)pyridin-4-ylmethylsulfanyl]-2-methyl-phenoxy}-acetic acid

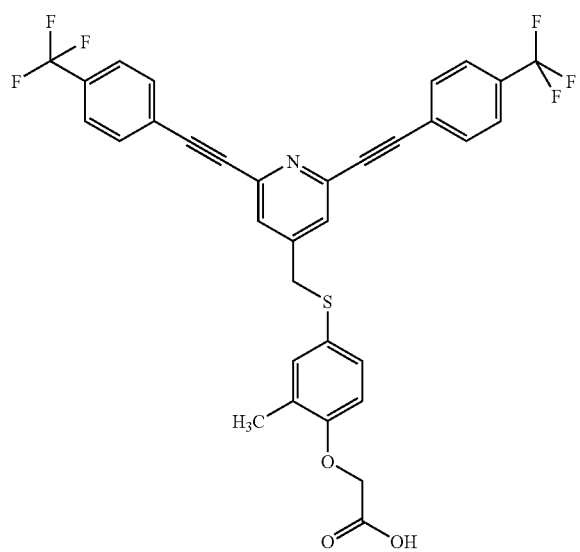

Example 19

{4-[2,6-Bis-(4-trifluoromethyl-phenylethynyl)-pyridin-4-ylmethoxy]-2-methyl-phenoxy}-acetic acid

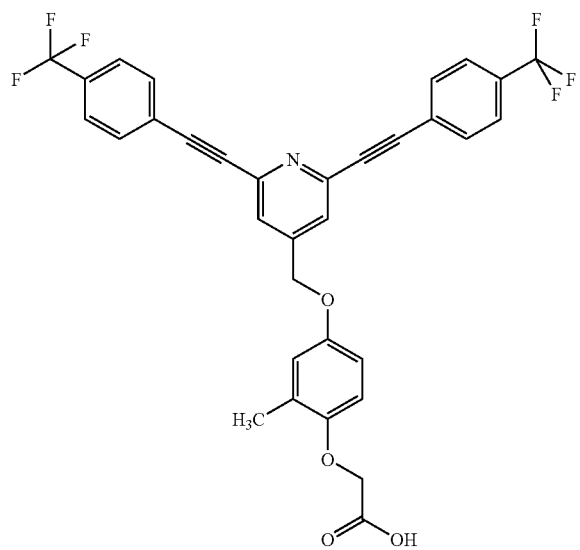

Example 20

{7-[2,6-Bis-(4-trifluoromethyl-phenylethynyl)-pyridin-4-ylmethylsulfanyl]-indan-4-yloxy}-acetic acid

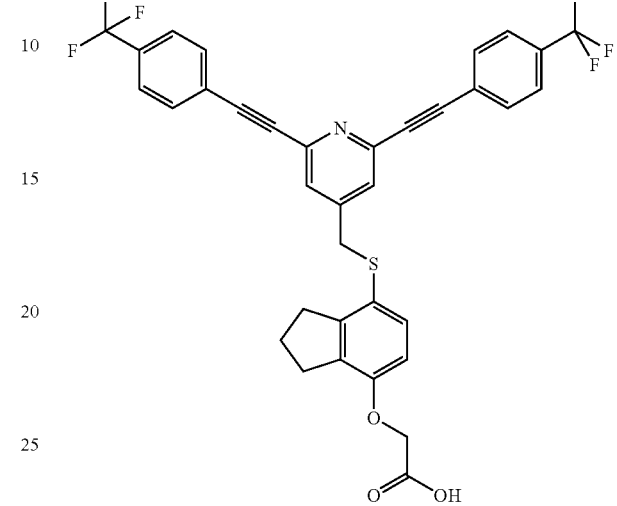

Example 21

{4-[3,5-Bis-(4-chloro-phenylethynyl)-benzyloxy]-2-methyl-phenoxy}-acetic acid

Pharmacological Methods
In Vitro PPARalpha, PPARgamma and PPARdelta Activation Activity The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50-80% at transfection. A total of 0.8 µg DNA containing 0.64 µg pM1α/βBD, 0.1 µg pCMVβGal, 0.08 µg pGL2(Gal4)$_5$ and 0.02 µg pADVANTAGE was transfected per well using FuGene transfection reagent according to the manufacturers instructions (Roche). Cells were allowed to express protein for 48 h followed by addition of compound.

Plasmids: Human PPAR α, γ and δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARα: aa 167—C-terminus; PPARγ: aa 165—C-terminus; PPARδ: aa 128—C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAGTACTGTCCTCCG(AG)) (Webster et al. (1988), Nucleic Acids Res. 16, 8192) into the vector pGL2 promotor (Promega) generating the plasmid pGL2(GAL4)$_5$. pCMVβ-Gal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments.

Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 µl supernatant from each transfection lysate was transferred to a new microplate. β-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

The invention claimed is:

1. A compound of formula (I) or a pharmaceutically acceptable salt thereof:

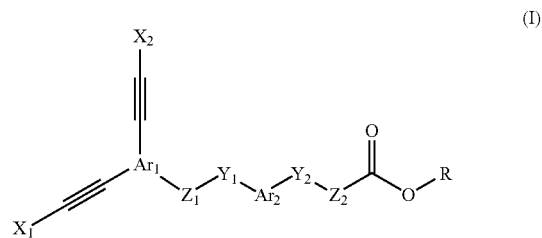

wherein $X_1$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted independently with one or more of halogen or hydroxy;

$X_2$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted independently with one or more of halogen or hydroxy;

$Ar_1$ is arylene or heteroarylene;

$Ar_2$ is arylene which is optionally substituted with one or more substituents, where said substituents independently are:

halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted independently with one or more halogens; or two of the substituents when placed in adjacent positions together with the atoms to which they are attached may form a five to eight member ring;

$Y_1$ is O or S;

$Y_2$ is O or S;

$Z_1$ is $(CH_2)_n$— wherein n is 0, 1, or 2;

$Z_2$ is —$(CH_2)_m$— wherein m is 1, 2 or 3; and

R is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl.

2. The compound according to claim 1, wherein $X_1$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted independently with one or more halogens; and $X_2$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted independently with one or more halogens.

3. The compound according to claim 1, wherein $X_1$ is aryl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more of halogen or hydroxy.

4. The compound according to claim 3, wherein $X_1$ is aryl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

5. The compound according to claim 3, wherein $X_1$ is aryl optionally substituted with one or more substituents, where said substituents independently are:

halogen; or $C_{1-6}$-alkyl or $C_{1-6}$-alkoxy, each of which is optionally substituted independently with one or more of halogen or hydroxy.

6. The compound according to claim 5, wherein $X_1$ is aryl optionally substituted with one or more substituents, where said substituents independently are:

halogen; or $C_{1-6}$-alkyl or $C_{1-6}$-alkoxy, each of which is optionally substituted independently with one or more halogens.

7. The compound according to claim 4, wherein $X_1$ is phenyl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more of halogen or hydroxy.

8. The compound according to claim 7, wherein $X_1$ is phenyl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

9. The compound according to claim 7, wherein $X_1$ is phenyl optionally substituted with one or more substituents, where said substituents independently are:

halogen; or $C_{1-6}$-alkyl or $C_{1-6}$-alkoxy, each of which is optionally substituted independently with one or more of halogen or hydroxy.

10. The compound according to claim 9, wherein $X_1$ is phenyl optionally substituted with one or more substituents, where said substituents independently are:

halogen; or $C_{1-6}$-alkyl or $C_{1-6}$-alkoxy, each of which is optionally substituted independently with one or more halogens.

11. The compound according to claim 1, wherein $X_1$ is heteroaryl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

12. The compound according to claim 11, wherein $X_1$ is heteroaryl optionally substituted with one or more substituents, where said substituents independently are:

halogen; or $C_{1-6}$-alkyl or $C_{1-6}$-alkoxy, each of which is optionally substituted independently with one or more halogens.

13. The compound according to claim 11, wherein $X_1$ is pyridyl, thiazolyl or pyrrolyl, each of which is optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

14. The compound according to claim 13, wherein $X_1$ is pyridyl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

15. The compound according to claim 14, wherein $X_1$ is pyridyl optionally substituted with one or more substituents, where said substituents independently are:

halogen; or $C_{1-6}$-alkyl or $C_{1-6}$-alkoxy, each of which is optionally substituted independently with one or more halogens.

16. The compound according to claim 12, wherein $X_1$ is thiazolyl or pyrrolyl, each of which is optionally substituted with one or more substituents, where said substituents independently are: selected from halogen; or $C_{1-6}$-alkyl or $C_{1-6}$-alkoxy, each of which is optionally substituted independently with one or more halogens.

17. The compound according to claim 1, wherein $X_2$ is aryl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more of halogen or hydroxy.

18. The compound according to claim 17, wherein $X_2$ is aryl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

19. The compound according to claim 17, wherein $X_2$ is aryl optionally substituted with one or more substituents, where said substituents independently are:
  halogen; or
  $C_{1-6}$-alkyl or $C_{1-6}$-alkoxy, each of which is optionally substituted independently with one or more of halogen or hydroxy.

20. The compound according to claim 19, wherein $X_2$ is aryl optionally substituted with one or more substituents, where said substituents independently are:
  halogen; or
  $C_{1-6}$-alkyl or $C_{1-6}$-alkoxy, each of which is optionally substituted independently with one or more halogens.

21. The compound according to claim 17, wherein $X_2$ is phenyl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more of halogen or hydroxy.

22. The compound according to claim 21, wherein $X_2$ is phenyl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

23. The compound according to claim 21, wherein $X_2$ is phenyl optionally substituted with one or more substituents, where said substituents independently are:
  halogen; or
  $C_{1-6}$-alkyl or $C_{1-6}$-alkoxy, each of which is optionally substituted independently with one or more of halogen or hydroxy.

24. The compound according to claim 23, wherein $X_2$ is phenyl optionally substituted with one or more substituents, where said substituents independently are:
  halogen; or
  $C_{1-6}$-alkyl or $C_{1-6}$-alkoxy, each of which is optionally substituted independently with one or more halogens.

25. The compound according to claim 1, wherein $X_2$ is heteroaryl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

26. The compound according to claim 25, wherein $X_2$ is heteroaryl optionally substituted with one or more substituents, where said substituents independently are:
  halogen; or
  $C_{1-6}$-alkyl or $C_{1-6}$-alkoxy, each of which is optionally substituted independently with one or more halogens.

27. The compound according to claim 25, wherein $X_2$ is pyridyl, thiazolyl or pyrrolyl, each of which is optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

28. The compound according to claim 27, wherein $X_2$ is pyridyl, optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted independently with one or more halogens.

29. The compound according to claim 28, wherein $X_2$ is pyridyl optionally substituted with one or more substituents, where said substituents independently are:
  halogen; or
  $C_{1-6}$-alkyl or $C_{1-6}$-alkoxy, each of which is optionally substituted independently with one or more halogens.

30. The compound according to claim 27, wherein $X_2$ is thiazolyl or pyrrolyl, each of which is optionally substituted with one or more substituents, where said substituents independently are: selected from halogen; or
  $C_{1-6}$-alkyl or $C_{1-6}$-alkoxy, each of which is optionally substituted independently with one or more halogens.

31. The compound according to claim 1, wherein $Ar_1$ is phenylene.

32. The compound according to claim 1, wherein $Ar_1$ is pyridylene.

33. The compound according to claim 1, wherein $Ar_2$ is phenylene which is optionally substituted with one or more substituents, where said substituents independently are:
  halogen, hydroxy or cyano; or
  $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted independently with one or more halogens; or
  two of the substituents when placed in adjacent positions together with the atoms to which they are attached may form a five to eight member ring.

34. The compound according to claim 33, wherein $Ar_2$ is phenylene which is optionally substituted with one or more substituents, where said substituents independently are:
  halogen; or
  $C_{1-6}$-alkyl, $C_{1-6}$-alkoxy, aryloxy or aralkoxy each of which is optionally substituted independently with one or more halogens; or
  two of the substituents when placed in adjacent positions together with the atoms to which they are attached may form a five-membered carbocycle.

35. The compound according to claim 33, wherein $Ar_2$ is phenylene which is optionally substituted with methyl.

36. The compound according to claim 1, wherein $Ar_2$ is indanylene.

37. The compound according to claim 1, wherein $Y_1$ is S.

38. The compound according to claim 1, wherein $Y_1$ is O.

39. The compound according to claim 1, wherein $Y_2$ is O.

40. The compound according to claim 1, wherein n is 0.

41. The compound according to claim 1, wherein m is 1.

42. The compound according to claim 1, wherein R is hydrogen or $C_{1-6}$-alkyl.

43. The compound according to claim 42, wherein R is hydrogen.

44. The compound according to claim 1, which is
{4-[3-(4-Chloro-phenylethynyl)-5-pyridin-2-ylethynyl-phenylsulfanyl]-2-methyl-phenoxy}-acetic acid;
[4-(3,5-Bis-pyridin-2-ylethynyl-phenylsulfanyl)-2-methyl-phenoxy]-acetic acid; or
{4-(3,5-Bis-(3-methoxy-phenylethynyl)-phenylsulfanyl]-2-methyl-phenoxy}-acetic acid; or a pharmaceutically acceptable salt thereof.

45. The compound according to claim 1, which is
[4-[3,5-Bis-[(thiazol-2-yl)ethynyl]phenylsulfanyl]-2-methylphenoxy]acetic acid;
[4-[3,5-Bis-(3,4-dimethoxyphenylethynyl)phenylsulfanyl]-2-methylphenoxy]acetic acid;
[4-[2,6-Bis-[(4-chlorophenyl)ethynyl]pyridine-4-ylsulfanyl]-2-methylphenoxy]acetic acid;
[4-[2,6-Bis[(2-pyridyl)ethynyl]pyridine-4-ylsulfanyl]-2-methylphenoxy]acetic acid;
[2-Methyl-4-[2-(2-pyridylethynyl)-6-[(4-trifluoromethylphenyl)ethynyl]pyridine-4-ylsulfan-yl]phenoxy]acetic acid;
[4-[3,5-Bis-(1-methyl-1H-pyrrol-2-ylethynyl)phenylsulfanyl]-2-methylphenoxy]acetic acid;
[2-Methyl-4-[2,6-bis[(4-trifluoromethylphenyl)ethynyl]pyridyl-4-sulfanyl]phenoxy]acetic acid;
{7-[2,6-Bis-(4-chloro-phenylethynyl)-pyridin-4-ylsulfanyl]-indan-4-yloxy}-acetic acid;
{7-[2,6-Bis-(4-hydroxymethyl-phenylethynyl)-pyridin-4-ylsulfanyl]-indan-4-yloxy}-acetic acid;
{4-[2,6-bis-(4-hydroxymethyl-phenylethynyl)-pyridin-4-ylsulfanyl]-2-methyl-phenoxy}-acetic acid;
{4-[2,6-bis-(2-hydroxymethyl-phenylethynyl)-pyridin-4-ylsulfanyl]-2-methyl-phenoxy}-acetic acid;
[4-[3,5-Bis-[(4-trifluoromethylphenyl)ethynyl]benzyloxy]-2-methylphenoxy]acetic acid;
[4-[3,5-Bis[(2-thienyl)ethynyl]benzyloxy]-2-methylphenoxy]acetic acid;
[4-[4,6-Bis[(4-trifluoromethylphenyl)ethynyl]pyridin-2-ylsulfanyl]-2-methylphenoxy]acetic acid;
{4-[2,6-Bis-(4-trifluoromethyl-phenylethynyl)-pyridin-4-ylmethylsulfanyl]-2-methyl-phenoxy}-acetic acid;
{4-[2,6-Bis-(4-trifluoromethyl-phenylethynyl)-pyridin-4-ylmethoxy]-2-methyl-phenoxy}-acetic acid;
{7-[2,6-Bis-(4-trifluoromethyl-phenylethynyl)-pyridin-4-ylmethylsulfanyl]-indan-4-yloxy}-acetic acid; or
{4-[3,5-Bis-(4-chloro-phenylethynyl)-benzyloxy]-2-methyl-phenoxy}-acetic acid;
or pharmaceutically acceptable salt thereof.

46. The compound according to claim 1, which is a PPARδ agonist.

47. The compound according to claim 46, which is a selective PPARδ agonist.

48. A pharmaceutical composition comprising a compound according to claim 1 and a pharmaceutically acceptable carrier or excipient.

49. The pharmaceutical composition according to claim 48 in unit dosage form, comprising from 0.05 mg to 1000 mg, from 0.1 to 500 mg, or from 0.5 mg to 200 mg per day of the compound.

50. The pharmaceutical composition according to claim 48 for oral, nasal, transdermal, pulmonal, or parenteral administration.

51. A method for the treatment of impaired glucose tolerance, syndrome X, or metabolic syndrome, the method comprising administering to a subject a compound according to claim 1.

52. The method according to claim 51, wherein the compound is administered to the subject in an amount from 0.05 mg to 1000 mg, from 0.1 to 500 mg, or from 0.5 mg to 200 mg per day.

* * * * *

UNITED STATES PATENT AND TRADEMARK OFFICE
CERTIFICATE OF CORRECTION

| | | |
|---|---|---|
| PATENT NO. | : 7,968,723 B2 | Page 1 of 1 |
| APPLICATION NO. | : 11/579712 | |
| DATED | : June 28, 2011 | |
| INVENTOR(S) | : Miroslav Havranek et al. | |

It is certified that error appears in the above-identified patent and that said Letters Patent is hereby corrected as shown below:

IN THE SPECIFICATIONS:

In column 1, line 10-12, after "May 5, 2004" delete "this application claims priority under 35 U.S.C. § 119(e) of U.S. Provisional Application 60/570,624, filed May 13, 2004.".

IN THE CLAIMS:

In column 53, line 3, in claim 1, delete "$(CH_2)_n$–" and insert -- –$(CH_2)_n$– --, therefor.

In column 54, line 64, in claim 16, after "are:" delete "selected from".

In column 56, line 26, in claim 30, after "are:" delete "selected from".

In column 57, line 8, in claim 44, delete "{4-(3,5-" and insert -- {4-[3,5- --, therefor.

In column 57, line 22, in Claim 45, delete "-ylsulfan-yl]" and insert -- -ylsulfanyl] --, therefor.

Signed and Sealed this
Sixth Day of September, 2011

David J. Kappos
*Director of the United States Patent and Trademark Office*